United States Patent
Arnould

(10) Patent No.: US 7,186,745 B2
(45) Date of Patent: Mar. 6, 2007

(54) INDOLONE DERIVATIVES HAVING VASCULAR DAMAGING ACTIVITY

(75) Inventor: Jean-Claude Arnould, Reims (FR)

(73) Assignee: AstraZeneca AB, Sodertalje (SE)

(*) Notice: Subject to any disclaimer, the term of this patent is extended or adjusted under 35 U.S.C. 154(b) by 272 days.

(21) Appl. No.: 10/469,834

(22) PCT Filed: Mar. 4, 2002

(86) PCT No.: PCT/GB02/00947

§ 371 (c)(1),
(2), (4) Date: Jan. 16, 2004

(87) PCT Pub. No.: WO02/070478

PCT Pub. Date: Sep. 12, 2002

(65) Prior Publication Data
US 2004/0147589 A1    Jul. 29, 2004

(30) Foreign Application Priority Data
Mar. 6, 2001 (EP) .................. 01400583

(51) Int. Cl.
A61K 31/40    (2006.01)
C07D 235/24    (2006.01)

(52) U.S. Cl. .................... 514/418; 548/306.4
(58) Field of Classification Search ............. 514/418; 548/306.4
See application file for complete search history.

(56) References Cited

U.S. PATENT DOCUMENTS

| | | |
|---|---|---|
| 3,975,531 A | 8/1976 | Welstead, Jr. et al. |
| 4,006,161 A | 2/1977 | Holmes et al. |
| 4,045,576 A | 8/1977 | Welstead, Jr. et al. |
| 4,182,774 A | 1/1980 | Welstead, Jr. et al. |
| 4,472,433 A | 9/1984 | Ueda et al. |
| 4,503,073 A | 3/1985 | Walsh et al. |
| 4,710,510 A | 12/1987 | Mertens et al. |
| 4,725,616 A | 2/1988 | Kadin |
| 4,791,129 A | 12/1988 | Kadin |
| 4,810,801 A | 3/1989 | Mertens et al. |
| 4,904,575 A | 2/1990 | Ono et al. |
| 5,047,554 A | 9/1991 | Ehrgott et al. |
| 5,290,802 A | 3/1994 | Ehrgott et al. |
| 5,310,935 A | 5/1994 | Brossi et al. |
| 5,382,593 A | 1/1995 | Le Baut et al. |
| 5,792,783 A | 8/1998 | Tang et al. |
| 5,834,504 A | 11/1998 | Tang et al. |
| 5,849,756 A | 12/1998 | Burger et al. |
| 5,883,113 A | 3/1999 | Tang et al. |
| 5,883,116 A | 3/1999 | Tang et al. |
| 5,886,020 A | 3/1999 | Tang et al. |
| 5,973,165 A | 10/1999 | Kuo et al. |
| 5,998,463 A | 12/1999 | Hulin et al. |
| 6,114,371 A | 9/2000 | Tang et al. |
| 6,174,883 B1 | 1/2001 | Ehrgott et al. |
| 6,225,335 B1 | 5/2001 | Tang et al. |
| 2001/0027207 A1 | 10/2001 | Tang et al. |

FOREIGN PATENT DOCUMENTS

| | | |
|---|---|---|
| AT | 339294 | 10/1977 |
| AU | 7509773 | 2/1977 |
| AU | 8659847 | 4/1987 |
| DE | 2159362 | 11/1971 |

(Continued)

OTHER PUBLICATIONS

Murata, S., et al., "Absorption, Distribution, Metabolism, and Excretion of Amfenac Sodium IV. Metabolic Fate in Man, Rat and Dog," Iyakuhin Kenkyu, 16(4), 769-783 (1985).

(Continued)

Primary Examiner—Deborah C. Lambkin

(57) ABSTRACT

This invention relates to the use of compounds of Formula (I) as vascular damaging agents: wherein X is selected from: —O—, —S—, —S(O)—, —S(O$_2$)—, —N(R$_5$)—, —C(O)—, —C(O)N(R$_5$)—, —N(R$_5$)C(O)—, —S(O2)N(R$_5$)—, or —N(R$_5$)S(O$_2$)—; R$_1$ is independently selected from: amino, halo, hydroxy, —OPO$_3$H$_2$, C$_{1-4}$alkyl, or C$_{1-4}$alkoxy, wherein the amino group is optionally substituted by an amino acid residue and the hydroxy group is optionally esterified; R$_2$ is selected from: hydrogen or C$_{1-4}$alkyl; R$_3$ is selected from: hydrogen, halo, hydroxy, hydroxyC$_{1-4}$alkyl, cyano, cyanoC$_{1-4}$alkyl, carboxy, carboxyC$_{1-4}$alkyl, C$_{1-4}$alkanoyl, C$_{1-4}$alkanoylC$_{1-4}$alkyl, carbamoyl, carbamoylC$_{1-4}$alkyl, C$_{1-4}$alkoxy, C$_{1-4}$alkoxycarbonyl, C$_{1-4}$alkoxycarbonylC$_{1-4}$alkyl, C$_{1-4}$alkoxycarbonylamino, amino, N—C$_{1-4}$alkylamino, NN-diC$_{1-4}$alkylamino, aminoC$_{1-4}$alkyl, N—C$_{1-4}$alkylaminoC$_{1-4}$alkyl, NN-diC$_{1-4}$alkylaminoC$_{1-4}$alkyl, ureido, or C$_{1-4}$alkylureyleno; R$_4$ is independently selected from: C$_{1-4}$alkyl, C$_{1-4}$alkoxy or halo; R$_5$ is selected from: hydrogen or C$_{1-4}$alkyl; n is 0 or 1; p is 0, 1, 2 or 3; and q is 0, 1 or 2; or a salt, pro-drug or solvate thereof. The invention also relates to novel compounds of Formula (I) and to processes for the preparation of compounds of Formula (I).

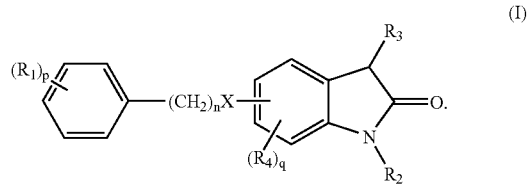

19 Claims, No Drawings

FOREIGN PATENT DOCUMENTS

| | | |
|---|---|---|
| DE | 199 40 829 A1 | 3/2001 |
| EP | 1 432 576 | 4/1976 |
| EP | 0 003 771 B1 | 9/1979 |
| EP | 1 560 007 | 1/1980 |
| EP | 0 008 226 B1 | 2/1980 |
| EP | 0 022 317 B1 | 1/1981 |
| EP | 2 098 208 | 11/1982 |
| EP | 0 153 818 B1 | 9/1985 |
| EP | 0 155 828 B1 | 9/1985 |
| EP | 0 164 860 B1 | 12/1985 |
| EP | 0 175 551 B1 | 3/1986 |
| EP | 0 181 136 B1 | 5/1986 |
| EP | 0 221 753 B1 | 5/1987 |
| EP | 0 249 407 B1 | 12/1987 |
| EP | 0 255 178 A2 | 2/1988 |
| EP | 0 350 163 A2 | 1/1990 |
| EP | 0 375 451 A2 | 6/1990 |
| EP | 0 393 936 B1 | 10/1990 |
| EP | 0 213 984 B1 | 1/1991 |
| EP | 0 438 796 B1 | 7/1991 |
| EP | 0 445 467 A1 | 9/1991 |
| EP | 0 459 133 A2 | 12/1991 |
| EP | 0 503 349 B1 | 9/1992 |
| EP | 0 275 762 B1 | 11/1993 |
| EP | 0 636 608 A1 | 7/1994 |
| EP | 0 673 937 A1 | 9/1995 |
| EP | 0 760 239 A2 | 3/1997 |
| EP | 0 788 890 A1 | 8/1997 |
| EP | 0 978 279 A1 | 2/2000 |
| EP | 1 136 071 A2 | 9/2001 |
| EP | 1 258 252 A1 | 11/2002 |
| GB | 2 042 541 | 9/1980 |
| GB | 2 055 820 | 3/1981 |
| GB | 2 105 708 | 3/1983 |
| GB | 2 253 848 | 9/1992 |
| GB | 2 272 439 | 5/1994 |
| IL | 48666 | 9/1979 |
| JP | 2000309534 | 11/2000 |
| WO | WO-91/09598 A1 | 7/1991 |
| WO | WO-92/16524 A1 | 10/1992 |
| WO | WO-93/12085 A1 | 6/1993 |
| WO | WO-93/15051 A1 | 8/1993 |
| WO | WO-94/05634 A1 | 3/1994 |
| WO | WO-94/13663 A1 | 6/1994 |
| WO | WO-94/18169 A1 | 8/1994 |
| WO | WO-94/27963 A1 | 12/1994 |
| WO | WO-94/29272 A1 | 12/1994 |
| WO | WO-95/07276 A1 | 3/1995 |
| WO | WO-95/14667 A1 | 6/1995 |
| WO | WO-96/02508 A1 | 2/1996 |
| WO | WO-96/02537 A1 | 2/1996 |
| WO | WO-96/40116 A1 | 12/1996 |
| WO | WO-97/06140 A1 | 2/1997 |
| WO | WO-97/11056 A1 | 3/1997 |
| WO | WO-97/42187 A1 | 11/1997 |
| WO | WO-98/49127 A1 | 11/1998 |
| WO | WO-98/50356 A1 | 11/1998 |
| WO | WO-99/10325 A1 | 3/1999 |
| WO | WO-99/48868 A1 | 9/1999 |
| WO | WO-99/65875 A1 | 11/1999 |
| WO | WO-99/61422 A1 | 12/1999 |
| WO | WO-00/08202 A2 | 2/2000 |
| WO | WO-00/12084 A1 | 3/2000 |
| WO | WO-00/24396 A2 | 5/2000 |
| WO | 00/41669 A2 | 7/2000 |
| WO | WO-00/54810 A1 | 9/2000 |
| WO | WO-00/56709 A1 | 9/2000 |
| WO | WO-01/56710 A1 | 9/2000 |
| WO | WO-00/59880 A1 | 10/2000 |
| WO | WO-01/02394 A1 | 1/2001 |
| WO | WO-01/37820 A2 | 5/2001 |
| WO | WO-01/47517 A1 | 7/2001 |
| WO | WO-01/047884 A1 | 7/2001 |
| WO | WO-01/57019 A1 | 8/2001 |
| WO | WO-01/60814 A2 | 8/2001 |
| WO | WO-01/64681 A2 | 9/2001 |
| WO | WO-01/68055 A1 | 9/2001 |
| WO | WO-01/072708 A2 | 10/2001 |
| WO | WO-01/94312 A2 | 12/2001 |

OTHER PUBLICATIONS

Isaka, M., et al., "Ocular Tissue Distribution in Rabbit after Instillation of Bromfenac Sodium Ophthalmic Solution," Yakubutsu Dotal, 14(1), 32-41 (1999).

Lewer, P., "Preparation of 7-Hydroxy-2-oxoindolin-3-ylacetic Acid and its [13C2], [5-nt-3H], and [5-n-3H]-7-O-Glucosyl Analogues for Use in the Study of Indol-3-yl-acetic Acid Catabolism," J. Chem. Soc. Perkin Trans., 1(4), 753-757 (1987).

Kametani, T., et al., "Studies on the Syntheses of Hetercyclic Compounds. Part 865. A Novel Synthesis of Indole Derivatives by Intramolecular Nucleophilic Aromatic Substitution," J. Chem. Soc. Perkin, 1(1), 290-294 (1981).

Baxter, I., et al., "The Oxidation of 5-Arylsulphonamido-3,3-dimethyloxindoles and Related Compounds," J. Chem. Soc. (C), 952-955 (1971).

Kametani, T., et al., "Synthesis of 1-Benzyloxindole Derivatives for the Study of Phenolic Oxidative Coupling (Studies on the Syntheses of Hyterocyclic Compounds. CCCXLVII," Chem. Pharm. Bull., 18(4), 645-650 (1970).

Kametani, T., et al., "A Novel Synthesis of Indole Derivatives," Heterocycles, 14(3), 277-280 (1980).

Lo, Y. S., et al., "Synthesis of 2-Amino-3-benzoylphenylacetic Acid," J. Heterocyclic Chem., 17, 1663-1664 (1980).

Goetz, F., et al., "Ring-Chain Tautomerism in Anions Derived from Substituted (Arylideneamino)toluenes and (Arylideneamino)oxindoles," J. Org. Chem., 48, 2468-2472 (1983).

Owa, T., et al., "A Focused Compound Library of Novel N-(7-Indolyl)benzenesulfonamides for the Discovery of Potent Cell Cycle Inhibitors," Bioorganic & Medicinal Chemistry Letters, 10, 1223-1226 (2000).

Walsh, D., et al., "Antiinflammatory Agents. 3. Synthesis and Pharmacological Evaluation of 2-Amino-3-benzoylphenylacetic Acid and Analogues," J. Med. Chem., 27(11), 1379-1388 (1984).

Kraynack, E., et al., "An Improved Procedure for the Regiospecific Synthesis of Electron Deficient 4- and 6-Substituted Isatins," Tetrahedron Letters, 39, 7679-7682 (1998).

Walsh, D., et al., "Antiinflammatory Agents. 2. Syntheses and Antiinflammatory Activity of Substituted 2-Aminophenylacetic Acid Derivatives," J. Med. Chem., 25, 446-451 (1982).

Walsh, D., et al., "Antiinflammatory Agents. 4. Syntheses and Biological Evaluation of Potential Prodrugs of 2-Amino-3-benzoylbenzeneacetic Acid and 2-Amino-3-(4-chlorobenzoyl)benzeneacetic Acid," J. Med. Chem., 33, 2296-2304 (1990).

Welstead, Jr., W. J., et al., "Antiinflammatory Agents. 1. Synthesis and Antiinflammatory Activity of 2-Amino-3-benzoylphenylacetic Acid," J. Med. Chem., 22(9), 1074-1079 (1979).

Lee, T.B.K., et al., "Asymmetric Alkylation of Oxindoles: An Approach to the Total Synthesis of (-)-Physostigmine," J. Org. Chem., 56, 872-875 (1991).

Jones, K.J., et al., "Aryl Radical Cyclisation Approach to Highly Substituted Oxindoles Related to Mitomycins," Tetrahedron Letters, 34(48), 7797-7798 (1993).

Karp, Gary M., "Regioselective Alkylationof Phenoxy-Substituted 3-(Methylthio)indolin-2(3H)-ones. Preparation of 3-, 1,3-, and 1,3,3-Substituted Indolin-2(3H)-ones," J. Org. Chem., 57, 4765-4772 (1992).

Dayan, F.E., et al., "Predicting the activity of the natural phytotoxic diphenyl ether cyperin using Comparative Molecular Field Analysis," Pest Manag. Sci., 56, 717-722 (2000).

Kato, Y., et al., "Simulaneous determination of amfenac sodium and its metabolite (7-benzoyl-2-oxindole) in human plasma by high-performance liquid chromatography,"J. Chromatography, 616, 67-71 (1993).

Osman, M.A., et al., "Determination of bromfenac in plasma by high-performance liquid chromatography," J. Chromatography, 489, 452-458 (1989).

Ruggli, P., et al., "Nitrogen heterocycles. XXIX. Derivatives of m- and p-phenylenediamines and of 5-amino.ovrddot.oxindole," Helvetica Chimica Acta, 20, 373-386 (1937).

K. Freter et al, Oxindole Analogs of (5-Hydroxy)-tryptamine and -trytophan and Inhibitors of the Biosynthesis and Breakdown of Serotonin, Journal of the American Chemical Society, 1958, 982-987, vol. 80.

Heather M. Nonhebel et al, Indole-3-acetic Acid Catabolism in Zea mays Seedlings, The Journal of Biological Chemistry, 1985, 12685-12689, 260 (23), USA.

EPO, Communication pursuant to Article 96(2) EPC issued by the EPO in relation to EP02702529.5, Nov. 8, 2005.

INDOLONE DERIVATIVES HAVING VASCULAR DAMAGING ACTIVITY

CROSS-REFERENCE TO RELATED APPLICATIONS

This application is a US National Stage under 35 U.S.C § 371 of International Application No. PCT/GB02/00947 (filed 4 Mar. 2002) which claims priority under 35 U.S.C. § 119(a)–(d) to Application No. EP 01400583.9 filed on 6 Mar. 2001.

This invention relates to vascular damaging agents and their uses. In particular it relates to certain novel compounds which may be of use as vascular damaging agents, to methods for preparing the compounds, to their use as medicaments (including in methods for the treatment of angiogenesis or disease states associated with angiogenesis) and to pharmaceutical compositions containing them. The invention also relates to the use of such compounds, and of certain analogous, known compounds in the manufacture of medicaments for the production of anti-angiogenic and/or anti-vascular effects.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Formation of new vasculature by angiogenesis is a key pathological feature of several diseases (J. Folkman, New England Journal of Medicine 333, 1757–1763 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy.

Reversal of neovascularisation by damaging the newly-formed vascular endothelium is therefore expected to have a beneficial therapeutic effect. Such vascular-damaging activity would clearly be of value in the treatment of disease states associated with angiogenesis such as cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

Certain known compounds that cause selective destruction of tumour vasculature have been reported, in vitro and at non-cytotoxic concentrations, to cause effects on proliferating endothelial cells, ie, cell detachment [Blakey D C et al, *Proceedings of the American Association for Cancer Research*, 41, 329, 2000 abstract 2086] and changes in cell shape [Davis P D et al, *Proceedings of the American Association for Cancer Research*, 41, 329, 2000 abstract 2085; Chaplin D J & Dougherty G J, *Br J Cancer*, 80, Suppl 1, 57–64, 1999]. It can therefore be expected that these compounds will have damaging effects on newly-formed vasculature, for example the vasculature of tumours. It can reasonably be predicted, for example, that they will be capable of causing selective destruction of tumour vasculature, both in vitro and in vivo. Destruction of tumour vasculature in turn leads to a reduction in tumour blood flow and to tumour cell death due to starvation of oxygen and nutrients, ie, to anti-tumour activity [Davis P D et al; Chaplin D J & Dougherty G J; Blakey D C et al, all supra].

Compounds with this activity have also been described in International Patent Application WO 99/02166 (Angiogene Pharmaceuticals), International Patent Application WO00/40529 (Angiogene Pharmaceuticals) and International Patent Application WO 00/41669 (Angiogene Pharmaceuticals).

We have identified a novel class of compounds with vascular damaging activity. Thus, according to the first feature of the present invention there is provided the use of a compound of Formula (I) for the manufacture of a medicament to inhibit and/or reverse and/or alleviate symptom of angiogenesis and/or any disease state associated with angiogenesis, wherein:

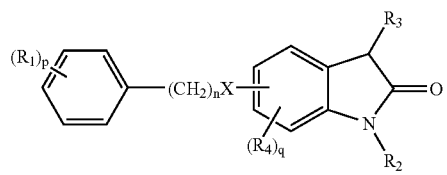

Formula (I)

X is selected from: —O—, —S—, —S(O)—, —S(O$_2$)—, —N(R$_5$)—, —C(O)—, —C(O)N(R$_5$)—, —N(R$_5$)C(O)—, —S(O$_2$)N(R$_5$)—, or —N(R$_5$)S(O$_2$)—;

R$_1$ is independently selected from: amino, halo, hydroxy, —OPO$_3$H$_2$, C$_{1-4}$alkyl, or C$_{1-4}$alkoxy, wherein the amino group is optionally substituted by an amino acid residue and the hydroxy group is optionally esterified;

R$_2$ is selected from: hydrogen or C$_{1-4}$alkyl;

R$_3$ is selected from: hydrogen, halo, hydroxy, hydroxyC$_{1-4}$alkyl, cyano, cyanoC$_{1-4}$alkyl, carboxy, carboxyC$_{1-4}$alkyl, C$_{1-4}$alkanoyl, C$_{1-4}$alkanoylC$_{1-4}$alkyl, carbamoyl, carbamoylC$_{1-4}$alkyl, C$_{1-4}$alkoxy, C$_{1-4}$alkoxycarbonyl, C$_{1-4}$alkoxycarbonylC$_{1-4}$alkyl, C$_{1-4}$alkoxycarbonylamino, amino, N—C$_{1-4}$alkylamino, N,N-diC$_{1-4}$alkylamino, aminoC$_{1-4}$alkyl, N—C$_{1-4}$alkylaminoC$_{1-4}$alkyl, N,N-diC$_{1-4}$alkylaminoC$_{1-4}$alkyl, ureido, or C$_{1-4}$alkylureyleno;

R$_4$ is independently selected from: C$_{1-4}$alkyl, C$_{1-4}$alkoxy or halo;

R$_5$ is selected from: hydrogen or C$_{1-4}$alkyl;

n is 0 or 1;

p is 0, 1, 2 or 3; and q is 0, 1 or 2;

or a salt, pro-drug or solvate thereof.

Whilst pharmaceutically acceptable salts of compounds of the invention are preferred, other non-pharmaceutically acceptable salts of compounds of the invention may be useful in the preparation of pharmaceutically-acceptable salts of compounds of the invention.

According to a further aspect of the first feature of the invention there is provided a method of treatment, in a warm-blooded animal, to inhibit and/or reverse and/or alleviate symptom of angiogenesis and/or any disease state associated with angiogenesis comprising administering to said warm-blooded animal a therapeutically (including prophylactically) effective amount of a compound of Formula (I), or a salt, pro-drug or solvate thereof.

Preferably a warm-blooded animal is a human.

According to a further aspect of the first feature of the invention there is provided a pharmaceutical composition comprising a compound of Formula (I), or a pharmaceutically-acceptable salt, pro-drug or solvate thereof, in admixture with a pharmaceutically-acceptable diluent or carrier, to inhibit and/or reverse and/or alleviate symptom of angiogenesis and/or any disease state associated with angiogenesis.

For the avoidance of doubt when p is 0, all positions on the phenyl ring are substituted by hydrogen and when q is 0 all positions on the aromatic ring of the oxindole ring are substituted by hydrogen except for the position to which the '$(R_1)_p$-Phenyl-$(CH_2)_n$—X—' group is attached.

For the avoidance of doubt the use of the term $(R_1)_p$ when p is between 1 and 3, means that there are 1, 2 or 3 $R^1$ substituents on the phenyl ring, which when p is 2 or 3 can be the same group or different groups. For example, where $(R_1)_p$ is 3-chloro-4-methoxy then p is 2 and the phenyl ring has a chloro group at the 3-position and a methoxy group at the 4-position, in relation to the —$(CH_2)_n X$— group, and for example, when $(R_1)_p$ is di-halo, then p is 2 and the phenyl ring has two halo substituents which may be the same group or different groups, wherein the halo groups occupy 2 positions on the phenyl ring.

In this specification the generic term 'alkyl' includes both straight-chain and branched-chain alkyl groups. However references to individual alkyl groups such as 'propyl' are specific for the straight-chain version only and references to individual branched-chain alkyl groups such as 'isopropyl' are specific for the branched-chain version only. An analogous convention applies to other generic terms.

The term halo refers to fluoro, chloro, bromo or iodo.

The term carbamoyl refers to —$C(O)NH_2$.

An amino acid residue is defined as that derived form the coupling of an L-amino acid with an amino group via an amide bond. This bond can either be formed via a carboxylate group on the amino acid backbone or via a side chain carboxylate group, preferably via carboxylate group on the amino acid backbone. Amino acid residues include those derived from natural and non-natural amino acids, preferably natural amino acids and include α-amino acids, β-amino acids and γ-amino acids. For the avoidance of doubt an amino acids include those with the generic structure:

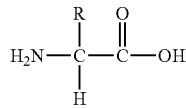

where R is the amino acid side chain: The definition of amino acid also includes amino acid analogues which have additional methylene groups within the amino acid backbone, for example β-alanine.

Preferred amino acids include glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine, histidine, β-alanine and ornithine. More preferred amino acids include glutamic acid, serine, threonine, arginine, glycine, alanine, β-alanine and lysine. Especially preferred amino acids include glutamic acid, serine, and glycine.

Preferably esterifying groups at $R_1$ are esterifying groups which increase the solubility of the molecule in water at a pH of approximately pH=7. Such groups included groups with ionisable groups, such as acidic functions or basic functions and groups containing a hydrophilic function. Basic functions include: amino, morpholino, piperidino, piperazino, pyrrolidino, amino acids and imidazolino. Acidic functions include: carboxy, sulphonic acid, phosphate, sulphate and acid mimetics such as tetrazolyl. Hydrophilic groups include hydroxyl.

Preferred $R_1$ groups wherein hydroxy is esterfied include: $C_{1-6}$alkanoyloxy, arylcarbonyloxy, heterocyclylcarbonyloxy, heteroarylcarbonyloxy wherein the $R_1$ group is optionally substituted with between 1 and 3 groups selected from $C_{1-4}$alkyl, $C_{1-4}$alkanoyl, $C_{1-4}$alkanoyl$C_{1-4}$alkyl, $C_{1-4}$alkanoylheterocyclyl, hydroxy, hydroxy$C_{1-4}$alkyl, carboxy, carboxyphenyl, phosphono, phosphono$C_{1-4}$alkyl, amino, amino$C_{1-4}$alkyl, N—$C_{1-4}$alkylamino, N,N-di$C_{1-4}$alkylamino, carbamoyl, carbamoyl$C_{1-4}$alkyl, heterocyclyl, heterocyclyl$C_{1-4}$alkyl, heterocyclylcarbonyl, heterocycl$C_{1-4}$alkanoylamino, carbamoylheterocyclyl, [wherein optional substituents comprising heterocyclyl are optionally further substituted by $C_{1-4}$alkyl, hydroxy$C_{1-4}$alkyl, $C_{1-4}$alkoxy$C_{1-4}$alkyl, $C_{1-4}$alkanoyl and formyl, wherein the carbamoyl and amino optional substituents are optionally further N-substituted by, $C_{1-4}$alkyl, di-$C_{1-4}$alkyl, hydroxy$C_{1-4}$alkyl, di-(hydroxy$C_{1-4}$alkyl), carboxy$C_{1-4}$alkyl, and wherein the amino group is optionally substituted by an amino acid residue] with the proviso that when $R_1$ is $C_{1-6}$alkanoyloxy or arylcarbonyloxy $R_1$ is not unsubstituted and $R_1$ is not substituted by $C_{1-4}$alkyl.

More preferred $R_1$ groups wherein hydroxy is esterfied include: carboxypentanoyloxy,
4-carboxyphenylpropanoyloxy 4-(N-methylpiperizin-1-ylethyl)phenylcarbonyloxy,
4-(piperizin-1-ylethyl)phenylcarbonyloxy, 4-[N-di-(hydroxyethyl)aminomethyl]phenylcarbonyloxy,
3-(N-acetylpiperizin-1-ylethyl)phenylcarbonyloxy,
3-[N-di-(hydroxyethyl)aminomethyl]phenylcarbonyloxy,
4-(N-methylpiperizin-1-ylpropanoylamino)phenylcarbonyloxy,
N-methylpiperizin-1-ylcarbonylpropanoyloxy,
N-di-(hydroxyethyl)aminocarbonylpropanoyloxy, piperizin-1-ylcarbonylpropanoyloxy,
(N-acetylpiperizin-1-yl)carbonylpropanoyloxy, (N-di-(hydroxyethyl)aminocarbonylpropanoyloxy, and 4(piperizin-1-ylmethyl)phenylcarbonyloxy.

Further preferred $R_1$ groups wherein hydroxy is esterfied include:
4-(N-methylpiperizin-1-ylpropanoylamino)phenylcarbonyloxy,
N-methylpiperizin-1-ylcarbonylpropanoyloxy and
N-di-(hydroxyethyl)aminocarbonylpropanoyloxy.

Examples of $C_{1-4}$alkyl include methyl, ethyl, propyl, isopropyl, sec-butyl and tert-butyl, examples of hydroxy$C_{1-4}$alkyl include hydroxymethyl, hydroxyethyl and hydroxypropyl, examples of amino$C_{1-4}$alkyl include aminomethyl, aminoethyl or aminopropyl, examples of cyano$C_{1-4}$alkyl include cyanomethyl, cyanoethyl and cyanopropyl, examples of carboxy$C_{1-4}$alkyl include carboxymethyl, carboxyethyl or carboxypropyl, examples of carbamoyl$C_{1-4}$alkyl include aminocarbonylmethyl, aminocarbonylethyl and aminocarbonypropyl, examples of $C_{1-4}$alkoxy include methoxy, ethoxy and propoxy, examples of $C_{1-4}$alkoxycarbonyl include methoxycarbonyl, tert-butoxycarbonyl, ethoxycarbonyl and propoxycarbonyl, examples of $C_{1-4}$alkoxycarbonyl$C_{1-4}$alkyl include methoxycarbonylmethyl, tert-butoxycarbonylethyl, ethoxycarbonylmethyl and propoxycarbonylethyl, examples of $C_{1-4}$alkoxycarbonylamio include methoxycarbonylamino and t-butoxycarbonylamino, examples of $C_{1-4}$alkanoyl include acetyl, ethylcarbonyl and butylcarbonyl, examples of N—$C_{1-4}$alkylamino include N-methylamino and N-ethylamino, and examples of N,N-di$C_{1-4}$alkylamino include N,N-dimethylamino, N,N-diethylamino and N-methyl-N-ethylamino, examples of N—$C_{1-4}$alkylamino$C_{1-4}$alkyl include N-methylaminomethyl and N-ethylaminoethyl, examples of N,N-di-$C_{1-4}$alkylamino$C_{1-4}$alkyl include N,N-dimethylaminomethyl and N-methyl-N-ethylaminomethyl, examples of $C_{1-4}$alkylureyleno include methylureyleno, ethylureyleno or propylureyleno.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a carbazole derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with methylamine, dimethylamine, trimethylamine, piperidine, morpholine or tris-(2-hydroxyethyl)amine.

The compounds of the Formula (I) may be administered in the form of a pro-drug which is broken down in the human or animal body to give a compound of the Formula (I). Examples of pro-drugs include in-vivo hydrolysable esters of a compound of the Formula (I).

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An in-vivo hydrolysable ester of a compound of the Formula (I) containing carboxy or hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the Formula (I) containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

It is to be understood that, insofar as certain of the compounds in the different features of the invention may exist in optically active or racemic forms by virtue of one or more asymmetric carbon atoms, the invention includes in its definition any such optically active or racemic form which possesses the property of inhibiting and/or reversing and/or alleviating the symptoms of angiogenesis and/or any disease states associated with angiogenesis. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of inhibiting and/or reversing and/or alleviating the symptoms of angiogenesis and/or any disease states associated with angiogenesis.

It will also be understood that certain compounds of the present invention may exist in solvated, for example hydrated, as well as unsolvated forms. It is to be understood that the present invention encompasses all such solvated forms which possess the property of the property of inhibiting and/or reversing and/or alleviating the symptoms of angiogenesis and/or any disease states associated with angiogenesis.

According to a second feature of the invention there is provided the use of a compound of Formula (II) as a medicament:

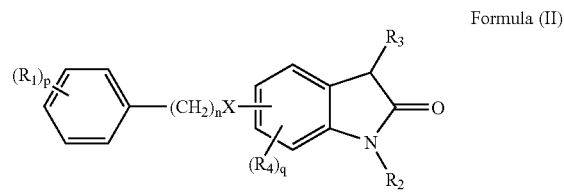

Formula (II)

X is selected from: —O—, —S—, —S(O)—, —S($O_2$)—, —N($R_5$)—, —C(O)—, —C(O)N($R_5$)—, —N($R_5$)C(O)—, —S($O_2$)N($R_5$)—, or —N($R_5$)S($O_2$)—;
$R_1$ is independently selected from: amino, halo, hydroxy, —OP$O_3H_2$, $C_{1-4}$alkyl, or $C_{1-4}$alkoxy, wherein the amino group is optionally substituted by an amino acid residue and the hydroxy group is optionally esterified;
$R_2$ is selected from: hydrogen or $C_{1-4}$alkyl;
$R_3$ is selected from: hydrogen, halo, hydroxy, hydroxy$C_{1-4}$alkyl, cyano, cyano$C_{1-4}$alkyl, carboxy, carboxy$C_{1-4}$alkyl, $C_{1-4}$alkanoyl, $C_{1-4}$alkanoyl$C_{1-4}$alkyl, carbamoyl, carbamoyl$C_{1-4}$alkyl, $C_{1-4}$alkoxy, $C_{1-4}$alkoxycarbonyl, $C_{1-4}$alkoxycarbonyl$C_{1-4}$alkyl, $C_{1-4}$alkoxycarbonylamino, amino, N—$C_{1-4}$alkylamino, NN-di$C_{1-4}$alkylamino, amino$C_{1-4}$alkyl, N—$C_{1-4}$alkylamino$C_{1-4}$alkyl, NN-di$C_{1-4}$alkylamino$C_{1-4}$alkyl, ureido, or $C_{1-4}$alkylureyleno;
$R_4$ is independently selected from: $C_{1-4}$alkyl, $C_{1-4}$alkoxy or halo;
$R_5$ is selected from: hydrogen or $C_{1-4}$alkyl;
n is 0 or 1;
p is 1, 2 or 3; and
q is 0, 1 or 2;

with the proviso that:
(i) when p is 1, $R_1$ cannot be halo or methyl, and when p is 2, $(R_1)_p$ cannot be di-halo or di-methyl;
(ii) when X is —S($O_2$)N($R_5$)—, —N($R_5$)S($O_2$)—, —N($R_5$)C(O)— or —C(O)—, n is 0 or 1, $R_2$ is hydrogen, $R_3$ is hydrogen, q is 0 or q is 1 and $R_4$ is 5-chloro and $R^5$ is hydrogen, then $(R_1)_p$ cannot be 2-methoxy, 3-methoxy, 4-methoxy, 4-nitro, 4-hydroxy, 4-amino, 3-chloro-4-methoxy or 3-chloro4-ethoxy; and
(ii) when X is linked at the 7-position of the oxindole ring, X is —O—, n is 0, $R_2$ is hydrogen, $R_3$ is hydrogen or methyl and q is 0, then $(R_1)_p$ cannot be 2-methoxy, 2-amino, or 3,4,5-tri-methoxy;or a pharmaceutically-acceptable salt, prodrug or solvate thereof.

According to a further aspect of the second feature of the invention there is provided a compound of Formula (IIa):

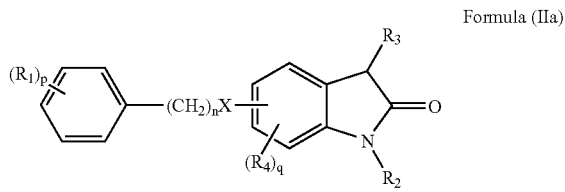

Formula (IIa)

wherein X, $R^1$, $R^2$, $R^3$, $R^4$, $R^5$, n, p and q are as defined for a compound of Formula (II);
with the proviso that:
(i) when p is 1, $R_1$ cannot be halo or methyl, and when p is 2, $(R_1)_p$ cannot be di-halo or di-methyl;
(ii) when X is —S($O_2$)N($R_5$)—, —N($R_5$)S($O_2$)—, —N($R_5$)C(O)— or —C(O)—, n is 0 or 1, $R_2$ is hydrogen, $R_3$ is hydrogen, q is 0 or q is 1 and $R_4$ is 5-chloro and $R^5$ is hydrogen, then $(R_1)_p$ cannot be 2-methoxy, 3-methoxy, 4-methoxy, 4-nitro, 4-hydroxy, 4-amino, 3-chloro4-methoxy or 3-chloro-4-ethoxy; and
(ii) when X is linked at the 7-position of the oxindole ring, X is —O—, n is 0, $R_2$ is hydrogen, $R_3$ is hydrogen or methyl and q is 0, then $(R_1)_p$ cannot be 2-methoxy, 2-amino, or 3,4,5-tri-methoxy;
or a pharmaceutically-acceptable salt, pro-drug or solvate thereof.

According to a further aspect of the second feature of the invention there is provided a pharmaceutical composition comprising a compound of Formula (II) or Formula (IIa), or pharmaceutically-acceptable salt, pro-drug or solvate.

According to a further aspect of the second feature of the invention there is provided a pharmaceutical composition comprising a compound of Formula (II) or Formula (IIa), or a pharmaceutically-acceptable salt, pro-drug or solvate thereof, in admixture with a pharmaceutically-acceptable diluent or carrier.

According to a third feature of the invention there is provided a compound of Formula (III), wherein:

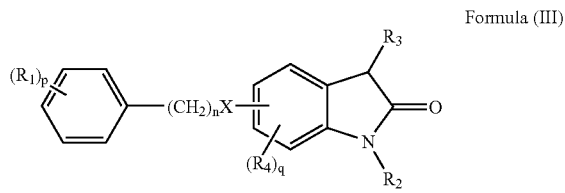

Formula (III)

X is selected from: —S—, —S(O)—, or —S($O_2$)—;
$R_1$ is independently selected from: amino, halo, hydroxy, —OP$O_3$$H_2$, $C_{1-4}$alkyl, or $C_{1-4}$alkoxy, wherein the amino group is optionally substituted by an amino acid residue and the hydroxy group is optionally esterified;
$R_2$ is selected from: hydrogen or $C_{1-4}$alkyl;
$R_3$ is selected from: hydrogen, halo, hydroxy, hydroxy$C_{1-4}$alkyl, cyano, cyano$C_{1-4}$alkyl, carboxy, carboxy$C_{1-4}$alkyl, $C_{1-4}$alkanoyl, $C_{1-4}$alkanoyl$C_{1-4}$alkyl, carbamoyl, carbamoyl$C_{1-4}$alkyl, $C_{1-4}$alkoxy, $C_{1-4}$alkoxycarbonyl, $C_{1-4}$alkoxycarbonyl$C_{1-4}$alkyl, $C_{1-4}$alkoxycarbonylamino, amino, N—$C_{1-4}$alkylamino, NN-di$C_{1-4}$alkylamino, amino$C_{1-4}$alkyl, N—$C_{1-4}$alkylamino$C_{1-4}$alkyl, NN-di$C_{1-4}$alkylamino$C_{1-4}$alkyl, ureido, or $C_{1-4}$alkylureyleno;
$R_4$ is independently selected from: $C_{1-4}$alkyl, $C_{1-4}$alkoxy or halo;
n is 0 or 1;
p is 0, 1, 2 or 3; and
q is 0, 1 or 2;
with the proviso that the following compounds are excluded:
7-(phenylsulfanyl)-1,3-dihydro-2H-indol-2-one;
7-(2-chlorophenylsulfanyl)-1,3-dihydro-2H-indol-2-one;
7-(4-chlorophenylsulfanyl)-1,3-dihydro-2H-indol-2-one;
7-(benzylsulfanyl)-1,3-dihydro-2H-indol-2one;
7-(phenylsulfinyl)-1,3-dihydro-2H-indol-2-one;
7-(2-chlorophenylsulfinyl)-1,3-dihydro-2H-indol-2-one;
7-(4-chlorophenylsulfinyl)-1,3-dihydro-2H-indol-2-one;
7-(phenylsulfonyl)-1,3-dihydro-2H-indol-2-one; and
7-(4chlorophenylsulfonyl)-1,3-dihydro-2H-indol-2-one;
or pharmaceutically-acceptable salt, pro-drug or solvate thereof.

According to a further aspect of the third feature of the invention there is provided a compound of Formula (III); as defined above, with the proviso that:
when —(C$H_2$)$_n$X— is linked at the 7-position of the oxindole ring, n is 0 or 1, $R_2$ and $R_3$ are each independently hydrogen and q is 0, then p cannot be 0 and $(R_1)_p$ cannot be 2-chloro or 4-chloro;
or pharmaceutically-acceptable salt, pro-drug or solvate thereof.

According to a fourth feature of the invention there is provided a compound of Formula (IV), wherein:

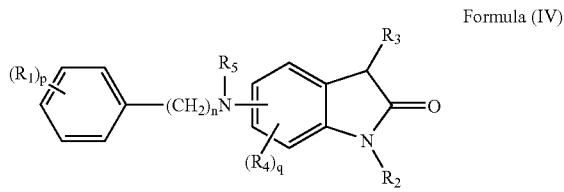

Formula (IV)

$R_1$ is independently selected from: amino, halo, hydroxy, —OP$O_3$$H_2$, $C_{1-4}$alkyl, or $C_{1-4}$alkoxy, wherein the amino group is optionally substituted by an amino acid residue and the hydroxy group is optionally esterified;
$R_2$ is selected from: hydrogen or $C_{1-4}$alkyl;
$R_3$ is selected from: hydrogen, halo, hydroxy, hydroxy$C_{1-4}$alkyl, cyano, cyano$C_{1-4}$alkyl, carboxy, carboxy$C_{1-4}$alkyl, $C_{1-4}$alkanoyl, $C_{1-4}$alkanoyl$C_{1-4}$alkyl, carbamoyl, carbamoyl$C_{1-4}$alkyl, $C_{1-4}$alkoxy, $C_{1-4}$alkoxycarbonyl, $C_{1-4}$alkoxycarbonyl$C_{1-4}$alkyl, $C_{1-4}$alkoxycarbonylamino, amino, N—$C_{1-4}$alkylamino, NN-di$C_{1-4}$alkylamino, aminoC$_{1-4}$alkyl, N—C$_{1-4}$alkylaminoC$_{1-4}$alkyl, NN-diC$_{1-4}$alkylaminoC$_{1-4}$alkyl, ureido, or C$_{1-4}$alkylureyleno;

R$_4$ is independently selected from: C$_{1-4}$alkyl, C$_{1-4}$alkoxy or halo;

R$_5$ is selected from: hydrogen or C$_{1-4}$alkyl;

n is 0 or 1;

p is 0, 1, 2 or 3; and q is 0, 1 or 2;

with the proviso that the following compounds are excluded:
5-(benzylamino)-1,3-dihydro-2H-indol-2-one;
7-anilino-1,3-dihydro-2H-indol-2-one;
7-(2-chloroanilino)-1,3-dihydro-2H-indol-2-one; and
7-(4-chloroanilino)-1,3-dihydro-2H-indol-2-one;

or pharmaceutically-acceptable salt, pro-drug or solvate thereof.

According to a further aspect of the fourth feature of the invention there is provided a compound of Formula (IV), as defined above, with the proviso that:
(i) when —(CH$_2$)$_n$N(R$_5$)— is linked at the 5-position of the oxindole ring, n is 1, R$_2$ and R$_3$ are each independently hydrogen and q is 0, then p cannot be 0; and
(ii) when —(CH$_2$)$_n$N(R$_5$)— is linked at the 7-position of the oxindole ring, n is 0, R$_2$ and R$_3$ are each independently hydrogen and q is 0, then p cannot be 0 and (R$_1$)$_p$ cannot be 2-chloro or 4-chloro;

or pharmaceutically-acceptable salt, pro-drug or solvate thereof.

According to a fifth feature of the invention there is provided a compound of Formula (V), wherein:

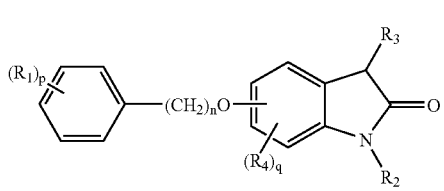

Formula (V)

R$_1$ is independently selected from: amino, halo, hydroxy, —OPO$_3$H$_2$, C$_{1-4}$alkyl, or C$_{1-4}$alkoxy, wherein the amino group is optionally substituted by an amino acid residue and the hydroxy group is optionally esterified;

R$_2$ is selected from: hydrogen or C$_{1-4}$alkyl;

R$_3$ is selected from: hydrogen, halo, hydroxy, hydroxyC$_{1-4}$alkyl, cyano, cyanoC$_{1-4}$alkyl, carboxy, carboxyC$_{1-4}$alkyl, C$_{1-4}$alkanoyl, C$_{1-4}$alkanoylC$_{1-4}$alkyl, carbamoyl, carbamoylC$_{1-4}$alkyl, C$_{1-4}$alkoxy, C$_{1-4}$alkoxycarbonyl, C$_{1-4}$alkoxycarbonylC$_{1-4}$alkyl, C$_{1-4}$alkoxycarbonylamino, amino, N—C$_{1-4}$alkylamino, NN-diC$_{1-4}$alkylamino, aminoC$_{1-4}$alkyl, N—C$_{1-4}$alkylaminoC$_{1-4}$alkyl, NN-diC$_{1-4}$alkylaminoC$_{1-4}$alkyl, ureido, or C$_{1-4}$alkylureyleno;

R$_4$ is independently selected from: C$_{1-4}$alkyl, C$_{1-4}$alkoxy or halo;

R$_5$ is selected from: hydrogen or C$_{1-4}$alkyl;

n is 0 or 1;

p is 0, 1, 2 or 3; and q is 0, 1 or 2;

with the proviso that:
(i) when —(CH$_2$)$_n$O— is linked at the 4-position of the oxindole ring, n is 0, p is 0 and R$_2$ and R$_3$ are each independently hydrogen and q is 1 then R$_4$ cannot be 7-chloro;
(ii) when —(CH$_2$)$_n$O— is linked at the 5-position of the oxindole ring, n is 0 or 1, R$_2$ is hydrogen or methyl, R$_3$ is hydrogen and q is 0, then p cannot be 0 and (R$_1$)$_p$ cannot be 2-chloro or chloro;
(iii) when —(CH$_2$)$_n$O— is linked at the 6-position of the oxindole ring, n is 1, p is 0, R$_2$ is hydrogen or methyl, R$_3$ is hydrogen and q is 1 then R$_4$ cannot be 5-methoxy; and
(iv) when —(CH$_2$)$_n$O— is linked at the 7-position of the oxindole ring, n is 0 or 1, R$_2$ is hydrogen or methyl, R$_3$ is hydrogen and q is 0, then p cannot be 0 and (R$_1$)$_p$ cannot be 2-chloro, 2-fluoro, 2-amino, 2,6-dichloro or 3,4,5-trimethoxy;

or pharmaceutically-acceptable salt, pro-drug or solvate thereof.

According to the sixth feature of the invention there is provided a compound of Formula (VI), wherein:

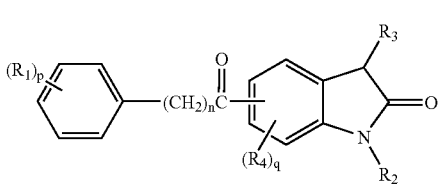

Formula (VI)

R$_1$ is independently selected from: amino, halo, hydroxy, —OPO$_3$H$_2$, C$_{1-4}$alkyl, or C$_{1-4}$alkoxy, wherein the amino group is optionally substituted by an amino acid residue and the hydroxy group is optionally esterified;

R$_2$ is selected from: hydrogen or C$_{1-4}$alkyl;

R$_3$ is selected from: hydrogen, halo, hydroxy, hydroxyC$_{1-4}$alkyl, cyano, cyanoC$_{1-4}$alkyl, carboxy, carboxyC$_{1-4}$alkyl, C$_{1-4}$alkanoyl, C$_{1-4}$alkanoylC$_{1-4}$alkyl, carbamoyl, carbamoylC$_{1-4}$alkyl, C$_{1-4}$alkoxy, C$_{1-4}$alkoxycarbonyl, C$_{1-4}$alkoxycarbonylC$_{1-4}$alkyl, C$_{1-4}$alkoxycarbonylamino, amino, N—C$_{1-4}$alkylamino, NN-diC$_{1-4}$alkylamino, aminoC$_{1-4}$alkyl, N—C$_{1-4}$alkylaminoC$_{1-4}$alkyl, NN-diC$_{1-4}$alkylaminoC$_{1-4}$alkyl, ureido, or C$_{1-4}$alkylureyleno;

R$_4$ is independently selected from: C$_{1-4}$alkyl, C$_{1-4}$alkoxy or halo;

R$_5$ is selected from: hydrogen or C$_{1-4}$alkyl;

n is 0 or 1;

p is 0, 1, 2 or 3; and q is 0, 1 or 2;

with the proviso that:
(i) when —(CH$_2$)$_n$C(O)— is linked at the 4-position of the oxindole ring, n is 0, p is 0, R$_2$ and R$_3$ are each independently hydrogen, then q cannot be 0;
(ii) when —(CH$_2$)$_n$C(O)— is linked at the 5-position of the oxindole ring, n is 0, R$_2$ is hydrogen or ethyl, R$_3$ is hydrogen or methoxycarbonyl and q is 0, then p cannot be 0 and (R$_1$)$_p$ cannot be 4-methyl, 4-chloro or 4-fluoro;
(iii) when —(CH$_2$)$_n$C(O)— is linked at the 6-position of the oxindole ring, n is 0, R$_2$ is hydrogen or ethyl, R$_3$ is hydrogen and q is 0, then p cannot be 0 and (R$_1$)$_p$ cannot be 4-methyl, 4-methoxy or 4-chloro;
(iv) when —(CH$_2$)$_n$C(O)— is linked at the 7-position of the oxindole ring, n is 0, R$_2$ is hydrogen, methyl or ethyl, R$_3$ is hydrogen, hydroxy, methoxycarbonyl, or ethoxycarbonyl, and q is 0 or q is 1 and R$_4$ is 4-methyl, 5-methyl, 6-methyl, 5-methoxy, 5-chloro, 6-chloro, 5-bromo or 5-fluoro, then p cannot be 0 and (R$_1$)$_p$ cannot be 2-methyl, 4-methyl, 4-methoxy, 4-hydroxy, 4-chloro, 4-bromo, 2-fluoro, 4-fluoro, 4-iodo, 2,4-dimethyl, 2,4-dichloro, 3,4-dichloro or 2-chloro-4-bromo;

or a salt, pro-drug or solvate thereof.

According to the seventh feature of the invention there is provided a compound of Formula (VII), wherein:

Formula (VII)

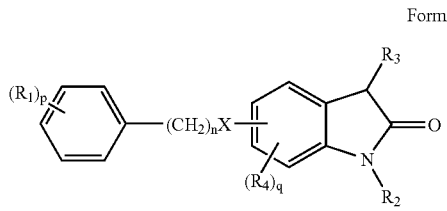

X is selected from: —C(O)N($R_5$)— or —N($R_5$)C(O)—;
$R_1$ is independently selected from: amino, halo, hydroxy, —OPO$_3$H$_2$, $C_{1-4}$alkyl, or $C_{1-4}$alkoxy, wherein the amino group is optionally substituted by an amino acid residue and the hydroxy group is optionally esterified;
$R_2$ is selected from: hydrogen or $C_{1-4}$alkyl;
$R_3$ is selected from: hydrogen, halo, hydroxy, hydroxyC$_{1-4}$alkyl, cyano, cyanoC$_{1-4}$alkyl, carboxy, carboxyC$_{1-4}$alkyl, $C_{1-4}$alkanoyl, $C_{1-4}$alkanoylC$_{1-4}$alkyl, carbamoyl, carbamoylC$_{1-4}$alkyl, $C_{1-4}$alkoxy, $C_{1-4}$alkoxycarbonyl, $C_{1-4}$alkoxycarbonylC$_{1-4}$alkyl, $C_{1-4}$alkoxycarbonylamino, amino, N—C$_{1-4}$alkylamino, NN-diC$_{1-4}$alkylamino, aminoC$_{1-4}$alkyl, N—C$_{1-4}$alkylaminoC$_{1-4}$alkyl, NN-diC$_{1-4}$alkylaminoC$_{1-4}$alkyl, ureido, or $C_{1-4}$alkylureyleno;
$R_4$ is independently selected from: $C_{1-4}$alkyl, $C_{1-4}$alkoxy or halo;
$R_5$ is selected from: hydrogen or $C_{1-4}$alkyl;
n is 0 or 1;
p is 0, 1, 2 or 3; and
q is 0, 1 or 2;
with the proviso that:
(i) when X is —N($R_5$)$_n$C(O)— linked at the 4-position of the oxindole ring, n is 0, $R_2$, $R_3$ and $R_5$ are each independently hydrogen and q is 0, then ($R_1$)$_p$ cannot be 4-methoxy, 3-chloro-4-methoxy or 3-chloro-4-ethoxy; and
(ii) when X is —C(O)N($R_5$)$_n$— linked at the 5-position of the oxindole ring, n is 0, p is 0, $R_2$, $R_3$ and $R_5$ are each independently hydrogen, then q cannot be 0, or a salt, pro-drug or solvate thereof.

According to the eight feature of the invention there is provided a compound of Formula (VIII), wherein:

Formula (VIII)

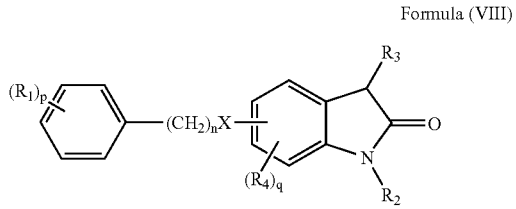

X is selected from: —S(O$_2$)N($R_5$)— or —N($R_5$)S(O$_2$)—;
$R_1$ is independently selected from: amino, halo, hydroxy, —OPO$_3$H$_2$, $C_{1-4}$alkyl, or $C_{1-4}$alkoxy, wherein the amino group is optionally substituted by an amino acid residue and the hydroxy group is optionally esterified;
$R_2$ is selected from: hydrogen or $C_{1-4}$alkyl;
$R_3$ is selected from: hydrogen, halo, hydroxy, hydroxyC$_{1-4}$alkyl, cyano, cyanoC$_{1-4}$alkyl, carboxy, carboxyC$_{1-4}$alkyl, $C_{1-4}$alkanoyl, $C_{1-4}$alkanoylC$_{1-4}$alkyl, carbamoyl, carbamoylC$_{1-4}$alkyl, $C_{1-4}$alkoxy, $C_{1-4}$alkoxycarbonyl, $C_{1-4}$alkoxycarbonylC$_{1-4}$alkyl, $C_{1-4}$alkoxycarbonylamino, amino, N—C$_4$alkylamino, NN-diC$_{1-4}$alkylamino, aminoC$_{1-4}$alkyl, N—C$_{1-4}$alkylaminoC$_{1-4}$alkyl, NN-diC$_{1-4}$alkylaminoC$_{1-4}$alkyl, ureido, or $C_{1-4}$alkylureyleno;
$R_4$ is independently selected from: $C_{1-4}$alkyl, $C_{1-4}$alkoxy or halo;
$R_5$ is selected from: hydrogen or $C_{1-4}$alkyl;
n is 0 or 1;
p is 0, 1, 2 or 3; and
q is 0, 1 or 2;
with the proviso that the following compounds are excluded:
  4-(4-methylbenzenesulphonamido)-1,3-dihydro-2H-indol-2-one;
  5-benzenesulphonamido-1,3-dihydro-2H-indol-2-one;
  5-(4-methylbenzenesulphonamido)-1,3-dihydro-2H-indol-2-one;
  N-methyl-5-(4-methylbenzenesulphonamido)-1,3-dihydro-2H-indol-2-one;
  N-methyl-5-(N-methyl-4-methylbenzenesulphonamido)-1,3-dihydro-2H-indol-2-one;
  6-(4-methylbenzenesulphonamido)-1,3-dihydro-2H-indol-2-one;
  6-(N-methyl-4-methylbenzenesulphonamido)-1,3-dihydro-2H-indol-2-one;
  7-(4-methylbenzenesulphonamido)-1,3-dihydro-2H-indol-2-one;
  6-(4-methoxybenzenesulphonamido)-1,3-dihydro-2H-indol-2-one;
  6-(4-aminobenzenesulphonamido)-1,3-dihydro-2H-indol-2-one; and
  6-(4-chlorobenzenesulphonamido)-1,3-dihydro-2H-indol-2-one;
or a salt pro-drug or solvate thereof.

According to a further aspect of the eighth feature of the invention there is provided a compound of Formula (VIII), as defined above, with the proviso that:
(i) when X is —S(O$_2$)N($R_5$)— linked at the 4 position of the oxindole ring, n is 0, $R_2$ and $R_3$ are each independently hydrogen, q is 0, and $R_5$ is hydrogen, then ($R_1$)$_p$ cannot be 4-methyl;
(ii) when X is —S(O$_2$)N($R_5$)— linked at the 5 position of the oxindole ring, n is 0, $R_2$ is hydrogen or methyl, $R_3$ is hydrogen, q is 0 and $R_5$ is hydrogen or methyl, then ($R_1$)$_p$ cannot be 4-methyl;
(iii) when X is —N($R_5$)S(O2)— linked at the 5-position of the oxindole ring, n is 0 or 1, R$^2$and R$^3$ are each independently hydrogen, q is 0 and R$^5$ is hydrogen, methyl or ethyl, then p cannot be 0 and ($R_1$)$_p$ cannot be 3-methyl, 2-methoxy, 3-methoxy, 3 chloro, 4-fluoro, or 2-fluoro—4-chloro.
(iv) when X is —S(O$_2$)N($R_5$)— linked at the 6 position of the oxindole ring, n is 0, $R_2$ and $R_3$ are each independently hydrogen, q is 0 and $R_5$ is hydrogen or methyl, then ($R_1$)$_p$ cannot be 4-methyl; and
(v) when X is —S(O$_2$)N($R_5$)— linked at the 7 position of the oxindole ring, n is 0, $R_2$ is hydrogen or methyl, $R_3$ is hydrogen, q is 0 and $R_5$ is hydrogen, then ($R_1$)$_p$ cannot be 4-methyl, 4-methoxy, 4-amino or 4-chloro;
or a salt, pro-drug or solvate thereof.

According to a further aspect of the third, fourth, fifth, sixth, seventh or eight feature of the invention there is provided the use of a compound of Formula (III), Formula (IV), Formula (V), Formula (VI), Formula (VII) or Formula (VIII) respectively, or pharmaceutically-acceptable salt, pro-drug or solvate thereof in the manufacture of a medicament to inhibit and/or reverse and/or alleviate symptom of angiogenesis and/or any disease state associated with angiogenesis, in a warm blooded animal.

According to a further aspect of the third, fourth, fifth, sixth, seventh or eight feature of the invention there is provided a pharmaceutical composition comprising a compound of Formula (III), Formula (IV), Formula (V), Formula (VI), Formula (VII) or Formula (VIII) respectively, or a pharmaceutically-acceptable salt, pro-drug or solvate thereof, in admixture with a pharmaceutically-acceptable diluent or carrier for the treatment of a warm-blooded animal, to inhibit and/or reverse and/or alleviate symptom of angiogenesis and/or any disease state associated with angiogenesis.

A preferred group of values of X in each feature of the invention is —O—, —S—, —S(O)—, —S($O_2$)—, or —N($R_5$)—. Preferably X is —O—, —S— or —N($R_5$)—. Most preferably X is —O— or —S—.

Preferably when n is 0, X is linked at the 5-position of the indole ring.

Preferably when n is 1, X is linked at the 6-position of the indole ring.

A preferred group of values of $R_1$ in each feature of the invention is hydrogen, amino, hydroxy, methyl or methoxy wherein the amino group is optionally substituted by an amino acid and the hydroxy group is optionally esterified. Preferably $R_1$ is hydrogen, amino, hydroxy, glutaminylamino, serylamino, alanylamino, glycylamino or —$PO_3H_2$, wherein the hydroxy group is optionally esterified. More preferably $R_1$ is hydrogen, amino, hydroxy, glutaminylamino, serylamino, glycylamino or —$PO_3H_2$.

A preferred group of values of $R_2$ in each feature of the invention is hydrogen, methyl or ethyl; Preferably $R_2$ is hydrogen or methyl.

A preferred group of values of $R_3$ in each feature of the invention is hydrogen, carbamoyl, or $C_{1-4}$alkylcarbamoyl. Preferably $R_3$ is hydrogen.

A preferred group of values of $R_4$ in each feature of the invention is hydrogen or $C_{1-4}$alkyl. Preferably hydrogen.

A preferred group of compound of each feature of the invention described herein; comprise compounds wherein: X is —O—.

A further preferred group of compound of each feature of the invention described herein; comprise compounds wherein:
X is —N—.

A further preferred group of compound of each feature of the invention described herein; comprise compounds wherein:
X is —S—, —S(O)— or —S($O_2$)—, preferably —S—.

A further preferred group of compound of each feature of the invention described herein; comprise compounds wherein:
$R_1$ is amino, hydroxy or —$OPO_3H_2$, wherein the amino group is optionally substituted by an amino acid residue and the hydroxy group is optionally esterified.

A further preferred group of compound of each feature of the invention described herein; comprise compounds wherein:
$R_1$ is amino, hydroxy or —$OPO_3H_2$, wherein the amino group is optionally substituted by an amino acid residue and the hydroxy group is optionally esterified; and
$R_3$ is carbamoyl, or $C_{1-4}$alkylcarbamoyl.

Particular compounds of each feature of the invention are:
5-(phenylsulfanyl)-1,3-dihydro-2H-indol-2-one;
5-(4-aminophenoxy)-1,3-dihydro-2H-indol-2-one;
5-(4-aminophenylsulfanyl)-1,3-dihydro-2H-indol-2-one;
5-(4-hydroxyphenylsulfanyl)-1,3-dihydro-2H-indol-2-one; and
6-(3-aminobenzyloxy)-1,3-dihydro-2H-indol-2-one;
or a salt, pro-drug or solvate thereof More particular compounds of each feature of the invention are:
5-(4-N-glutaminylaminophenoxy)-1,3-dihydro-2H-indol-2-one;
5-(4-N-Serylaminophenoxy)-1,3-dihydro-2H-indol-2-one;
5-(4-N-Glycylaminophenoxy)-1,3-dihydro-2H-indol-2-one;
5-(4-N-glutaminylaminophenylsulfanyl-1,3-dihydro-2H-indol-2-one;
5-(3-N-glutaminylaminobenzyloxy)-1,3-dihydro-2H-indol-2-one; and
5-(4-phosphonophenylsulfanyl)-1,3-dihydro-2H-indol-2-one
or a salt, pro-drug or solvate thereof.

A compound of the invention or a pharmaceutically-acceptable salt, or solvate thereof, may be prepared by any process known to be applicable to the preparation of chemically related compounds. Such processes, when used to prepare a compound of the invention or a pharmaceutically-acceptable salt, or solvate thereof, are provided as a further feature of the invention and are illustrated by the following representative examples in which $R_1$, $R_2$, $R_3$, $R_4$, $R_5$, X, n, p and q have the same meaning as herein before defined. The reader is referred to Advanced Organic Chemistry, $4^{th}$ Edition, by Jerry March, published by John Wiley & Sons 1992, for general guidance on reaction conditions and reagents. The reader is referred to Protective Groups in Organic Synthesis $2^{nd}$ Edition, by Green et al, published by John Wiley & Sons for general guidance on protecting groups.

Thus, according to the ninth feature of the invention there is provided a process for preparing a compound of Formula (I), or salt, pro-drug or solvate thereof, which process (wherein n, p, q, X, $R_1$, $R_2$, $R_3$, $R_4$ and $R_5$ are unless otherwise specified as defined in Formula (I)) comprises:

a) for compounds of Formula (I) wherein X is —O—, —S— or —N($R_5$)—, reacting a compound of Formula (A) with a compound of Formula (B),

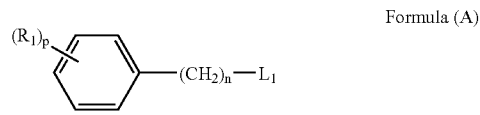

Formula (A)

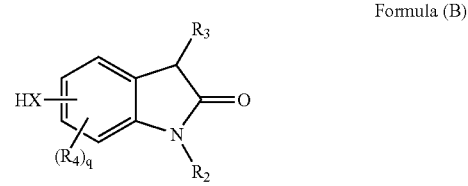

Formula (B)

wherein $L_1$ is a leaving group;

b) for compounds of Formula (I) wherein $R_2$ is hydrogen, reduction of a compound of Formula (C), wherein $R_6$ is hydrogen or an alkyl chain,

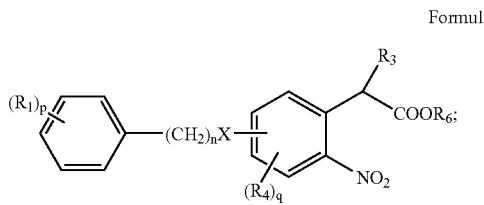

Formula (C)

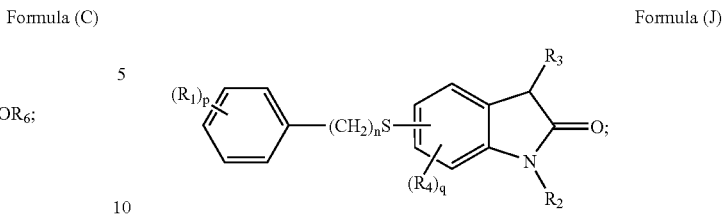

Formula (J)

c) for compounds of Formula (I) wherein $R_2$ is $C_{1-4}$alkyl, reacting a compound of Formula (I) wherein $R_2$ is hydrogen with a suitable alkylhalide;

d) for compounds of Formula (I) wherein $R_2$ is hydrogen and $R_3$ is hydrogen reacting a compound of Formula (D) with an alkylthioacetate, followed by reduction,

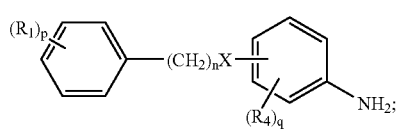

Formula (D)

e) for compounds of Formula (I) wherein X is —S($O_2$)N($R_5$)—, reacting a compound of Formula (E) with an amine of Formula (F),

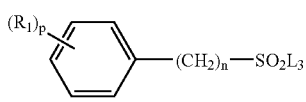

Formula (E)

Formula (F)

wherein $L_3$ is a displaceable group;

f) for compounds of Formula (I) wherein X is —N($R_5$)S($O_2$)—; reacting an amine of Formula (G) with a compound of Formula (H), Formula (G)

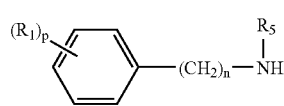

Formula (H)

wherein $L_3$ is a displaceable group;

g) for compounds of Formula (I) wherein X is —S(O)—, —S($O_2$)—, oxidising a compound of Formula (J), and thereafter if necessary:
i) converting a compound of the Formula (I) into another compound of the Formula (I);
ii) removing any protecting groups;
iii) forming a salt, pro-drug or solvate.

According to a further aspect of the ninth feature of the invention there is provided the processes a), b), c), d), e), f), and g) described above for the preparation of compounds of the Formula (II), Formula (III), Formula (IV), Formula (V), Formula (VI), Formula (VII) or Formula (VIII), or a salt, pro-drug or solvate thereof,.

Specific reaction conditions for the above reactions are as follows:

Process a) Compounds of Formula (A) and compound of Formula (B) can be reacted together in an organic solvent, at a temperature between room temperature and about 80° C., optionally in the presence of a base such as sodium hydride, potassium carbonate or triethylamine.

Process b) The conditions for reduction of a compound of Formula (C) are well known in the art. Examples of reducing agents include hydrogen and a hydrogenation catalyst (for example palladium on carbon), iron and acetic acid, and zinc and hydrochloric acid. The reaction is preferable carried out in the presence of a suitable solvent such as an alcohol, for example methanol or ethanol, and at a temperature in the range of 0–80° C., preferably at or near room temperature.

Process c) Compounds of Formula (I) wherein $R_2$ is hydrogen and a suitable alkylhaldie may be reacted together in a suitable organic solvent such as DMF or DMSO, in the presence of a base, such as sodium hydride or potassium carbonate at a temperature between about room temperature and about 80° C.

Process d) Compounds of Formula (D) can be reacted with a alkylthioacetate in the presence of $SO_2Cl_2$ and in the presence of a bases such as triethylamine, followed by reduction with a suitable reducing agent, such as Raney Nickel in a suitable polar solvent, such as ethanol or methanol at approximately room temperature.

Process e) and f) The reaction of compounds of Formula (E) and Formula (F) or the reaction of Formula (G) and Formula (H) where $L_3$ is a displaceable group is well known in the art, for example they may be reacted in the presence of a base, for example triethylamine, pyridine, or 2,6-di-alkyl-pyridines such as 2,6-lutidine or 2,6-di-tert-butylpyridine, and in a suitable solvent, such as DMA, DCM, benzene, THF and DMF. The reaction may conveniently be performed at a temperature in the range of −40 to 140° C.

Process g) The oxidization of a compound of Formula (J) is well known in the art, for example, reaction with metachloroperbenzoic acid (MCPBA) is the presence of a suitable solvent such as dichloromethane at ambient temperature. If an excess of MCPBA is used a S compound of Formula (I) wherein X is —S($O_2$)— is obtained.

Intermediates for the processes a), b), c) and d) can be prepared as outlined in Scheme 1, wherein P is protecting group, using the following reaction conditions:

Reaction Conditions (i) Reaction with chloroacetate in an organic solvent such as DMF or acetone, in the presence of a base such as sodium hydride or potassium carbonate at a temperature between approximately room temperature and approximately 80° C.

Reaction Conditions (ii) Reduction using a suitable reducing agent such as hydrogen and a hydrogenation catalyst (for example palladium on carbon), iron and acetic acid, or zinc and hydrochloric acid.

Reaction Conditions (iii) Reaction conditions for the removal of a protecting group are well know in the art.

The compounds used as starting points for the reactions described above are commercially available or they are known compounds or they are prepared by processes know in the art.

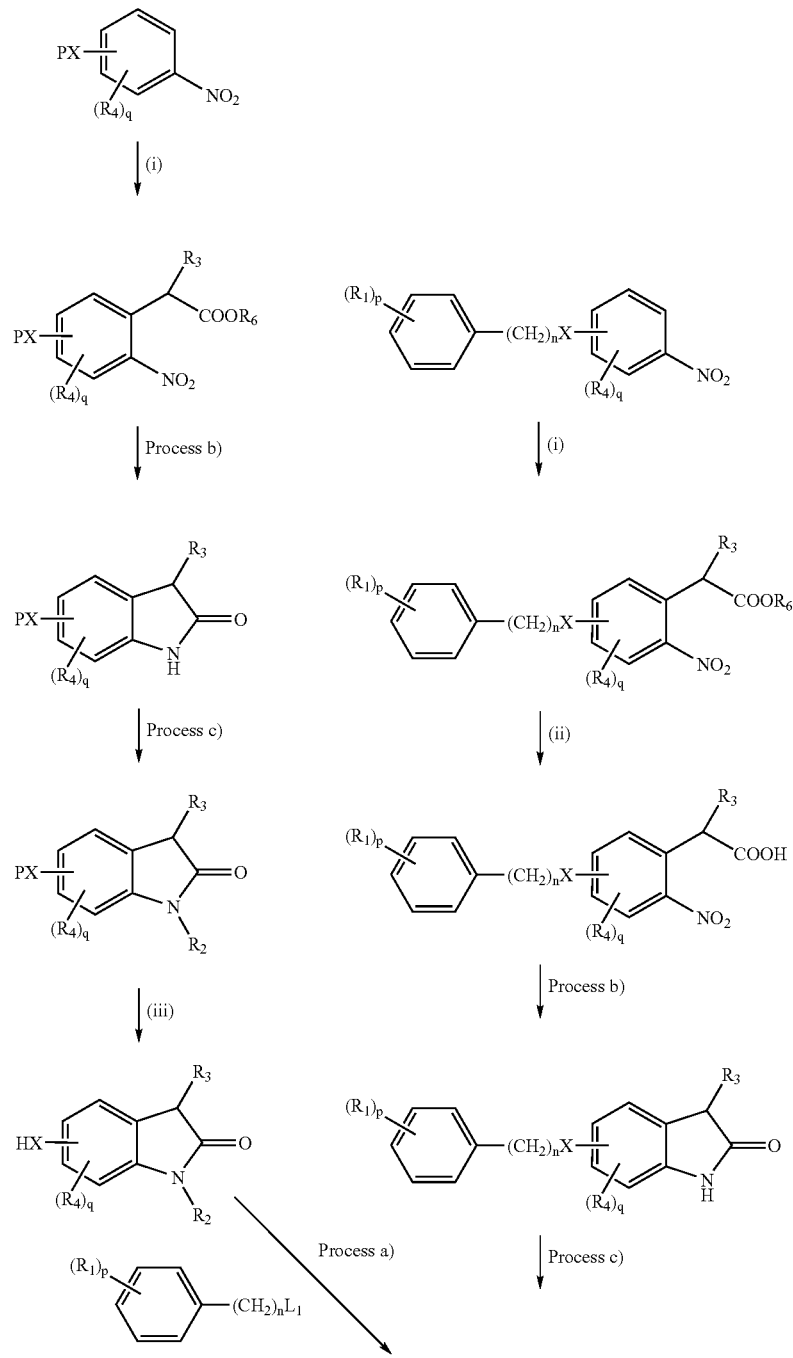

Scheme 1

-continued

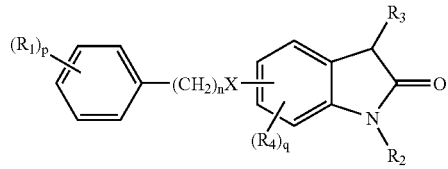

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

In order to use a compound of the Formula (I) or Formula (II) or Formula (III), Formula (IV), Formula (V), Formula (VI), Formula (VII) or Formula (VIII) or a pharmaceutically-acceptable salt or in vivo cleavable ester thereof, for the therapeutic treatment (including prophylactic treatment) of mammals including humans, it is normally formulated in accordance with standard pharmaceutical practice as a pharmaceutical composition.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I), Formula (II) or Formula (III), Formula (IV), Formula (V), Formula (VI), Formula (VII) or Formula (VIII) will naturally vary according to the nature and severity of the conditions, the age and sex of the animal or patient and the route of administration, according to well known principles of medicine.

In using a compound of the Formula (I), Formula (II), Formula (III), Formula (IV), Formula (V), Formula (VI), Formula (VII) or Formula (VIII) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 20 mg per kg body weight will generally be used. Intravenous administration is however preferred, typically, intravenous doses of about 10 mg to 500 mg per patient of a compound of this invention.

The compounds of this invention may be used in combination with other drugs and therapies used to inhibit and/or reverse and/or alleviate symptom of angiogenesis and/or any disease state associated with angiogenesis. Examples of such disease states include: cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

If formulated as a fixed dose such combination products employ the compounds of this invention within the dosage range described herein and the other pharmaceutically-active agent within its approved dosage range. Sequential use is contemplated when a combination formulation is inappropriate.

According to the tenth feature of the present invention there is provided a compound of Formula (I), Formula (II), Formula (III), Formula (IV), Formula (V), Formula (VI), formula (VII) or Formula (VIII), or salt, pro-drug or solvate thereof, preferably in the form of a pharmaceutical composition, when dosed in divided doses (also known as split doses) produces a greater anti-tumour effect than when a single dose is given.

Anti-tumour effects include but are not limited to, inhibition of tumour growth, tumour growth delay, regression of tumour, shrinkage of tumour, increased time to re-growth of tumour on cessation of treatment, slowing of disease progression. It is expected that when a method of treatment of the present invention is administered to a warm-blooded animal such as a human, in need of treatment for cancer involving a solid tumour, said method of treatment will produce an effect, as measured by, for example, one or more of: the extent of the anti-tumour effect, the response rate, the time to disease progression and the survival rate.

According to a further aspect of the tenth feature of the present invention there is provided a method for the production of a vascular damaging effect in a warm-blooded animal such as a human, which comprises administering to said animal in divided doses an effective amount of a compound of Formula (I), Formula (II), Formula (III), Formula (IV), Formula (V), Formula (VI), Formula (VII) or Formula (VIII), or salt, pro-drug or solvate thereof, preferably in the form of a pharmaceutical composition.

According to a further aspect of the tenth feature of the present invention there is provided a method for the treatment of a cancer involving a solid tumour in a warm-blooded animal such as a human, which comprises administering to said animal in divided doses an effective amount of a compound of Formula (I), Formula (II), Formula (III), Formula (IV), Formula (V), Formula (VI), Formula (VII) or Formula (VIII), or salt, pro-drug or solvate thereof, preferably in the form of a pharmaceutical composition.

According to a further aspect of the tenth feature of the present invention there is provided a medicament comprising two or more fractions of doses of a compound of Formula (I), Formula (II), Formula (III), Formula (IV), Formula (V), Formula (VI), Formula (VII) or Formula (VIII), or salt, pro-drug or solvate thereof, preferably in the form of a pharmaceutical composition, which together add up to a total daily dose, for administration in divided doses for use in a method of treatment of a human or animal body by therapy.

According to a further aspect of the tenth feature of the present invention there is provided a kit comprising two or more fractions of doses of a compound of Formula (I), Formula (II), Formula (III), Formula (IV), Formula (V), Formula (VI), Formula (VII) or Formula (VIII), or salt, pro-drug or solvate thereof, preferably in the form of a pharmaceutical composition, which together add up to a total daily dose, for administration in divided doses.

According to a further aspect of the tenth feature of the present invention there is provided a kit comprising:
a) two or more fractions of doses of a compound of Formula (I), Formula (II), Formula (III), Formula (IV), Formula (V), Formula (VI), Formula (VII) or Formula (VIII), or salt, pro-rug or solvate thereof, which together add up to a total daily dose, in unit dosage forms for administration in divided doses;
b) container means for containing said dosage forms.

According to a further aspect of the tenth feature of the present invention there is provided a kit comprising:
a) two or more fractions of doses of a compound of Formula (I), Formula (II), Formula (III), Formula (IV), Formula (V), Formula (VI), Formula (VII) or Formula (VIII), or salt, pro-drug or solvate thereof, which together add up to a total daily dose, together with a excipient or carrier, in unit dosage forms; and
b) container means for containing said dosage forms.

According to a further aspect of the tenth feature of the present invention there is provided the use of a compound of Formula (I), Formula (II), Formula (III), Formula (IV), Formula (V), Formula (VI), Formula (VII) or Formula (VIII), or salt, pro-drug or solvate thereof, in the manufacture of a medicament for administration in divided doses for use in the production of a vascular damaging effect in a warm-blooded animal such as a human.

According to a further aspect of the tenth feature of the present invention there is provided the use of a compound of Formula (I), Formula (II), Formula (III), Formula (IV), Formula (V), Formula (VI), Formula (VII) or Formula (VIII), or salt, pro-drug or solvate thereof, in the manufacture of a medicament for administration in divided doses for use in the production of an anti-cancer effect in a warm-blooded animal such as a human.

According to a further aspect of the tenth feature of the present invention there is provided the use of a compound of Formula (I), Formula (II), Formula (III), Formula (IV), Formula (V), Formula (VI), Formula (VII) or Formula (VIII), or salt, pro-drug or solvate thereof, in the manufacture of a medicament for administration in divided doses for use in the production of an anti-tumour effect in a warm-blooded animal such as a human.

Divided doses, also called split doses, means that the total dose to be administered to a warm-blooded animal, such as a human, in any one day period (for example one 24 hour period from midnight to midnight) is divided up into two or more fractions of the total dose and these fractions are administered with a time period between each fraction of about greater than 0 hours to about 10 hours, preferably about 1 hour to about 6 hours, more preferably about 2 hours to about 4 hours. The fractions of total dose may be about equal or unequal.

Preferably the total dose is divided into two parts which may be about equal or unequal.

The time intervals between doses may be for example selected from: about 1 hour, about 1.5 hours, about 2 hours, about 2.5 hours, about 3 hours, about 3.5 hours, about 4 hours, about 4.5 hours, about 5 hours, about 5.5 hours and about 6 hours.

The time intervals between doses may be any number (including non-integers) of minutes between greater than 0 minutes and 600 minutes, preferably between 45 and 375 minutes inclusive. If more than two doses are administered the time intervals between each dose may be about equal or unequal.

Preferably two doses are given with a time interval in between them of greater than or equal to 1 hour and less than 6 hours.

More preferably two doses are given with a time interval in between them of greater than or equal to two hours and less than 5 hours.

Yet more preferably two doses are given with a time interval in between them of greater than or equal to two hours and less than or equal to 4 hours.

Particularly the total dose is divided into two parts which may be about equal or unequal with a time interval between doses of greater than or equal to about two hours and less than or equal to about 4 hours.

More particularly the total dose is divided into two parts which may be about equal with a time interval between doses of greater than or equal to about two hours and less than or equal to about 4 hours.

For the avoidance of doubt the term 'about' in the description of time periods means the time given plus or minus 15 minutes, thus for example about 1 hour means 45 to 75 minutes, about 1.5 hours means 75 to 105 minutes. Elsewhere the term 'about' has its usual dictionary meaning.

Although the compounds of the Formula (I), Formula (II), Formula (III), Formula (IV), Formula (V), Formula (VI), Formula (VII) or Formula (VIII) are primarily of value as therapeutic agents for use in warm-blooded animals (including man), they are also useful whenever it is required to inhibit and/or reverse and/or alleviate symptom of angiogenesis and/or any disease state associated with angiogenesis. Thus, they are useful as pharmacological tools for use in the development of new biological tests and in the search for new pharmacological agents.

Biological Assay

Colchicine Binding Site Competitive Assay Kit.

The ability of a ligand to bind specifically to the colchicine binding site on tubulin, an indicator of the vascular damaging activity, was assessed using a size exclusion chromatography assay kit from "Cytoskeleton" (1650 Fillmore St. #240, Denver, Colo. 80206, U.S.A.) Catalogue number of kit: BK023.

The following reagents were used:
tubulin buffer, to give 0.1 mM GTP, 0.5 mM $MgCl_2$, 0.5 mM EGTA, 40 mM PIPES buffer at pH6.9 in the final reaction mix;
purified tubulin protein from bovine brain at 1 mg/ml in tubulin buffer;
0.02 mM fluorescent colchicine in tubulin buffer [FITC (fluorescein isothiocyanate)-labelled];
2 mM colchicine in tubulin buffer;
0.2 mM vinblastine in tubulin buffer; and
G-25 Sephadex™ Fine—particle size 34–138 μm.

The reaction was performed as follows: 8 μl of test compound (dissolved in DMSO) was gently mixed with 150 μl of tubulin. This was then incubated at 37° C. for 30 minutes. Then 4 μl of the fluorescent colchicine was added, the incubation mix vortexed for 5 seconds and then incubated for a further 30 minutes at 37° C. At the end of the reaction incubation size exclusion chromatography was performed to separate the tubulin with fluorescent colchicine bound from the free, unbound colchicine. If a test compound inhibited fluorescent colchicine binding then a reduced signal is measured and the compound is confirmed as a colchicine site binding moiety.

Chromatography was performed as follows, using chromatography columns filled with 3 mls of G-25 Sephadex™ Fine slurry. The incubation mixture was pipetted onto the column and up to 12 elutions of 160 μl were collected. The fluorescence of the tubulin-containing fractions was detected on a spectrophotometer which excites at 485 nm and emits at 535 nm. Control incubations were also performed, 8 μl DMSO (negative control) and 8 μl colchicine stock (positive competition control), instead of the 8 μl of test compound in the incubation mixture.

The degree of competition of colchicine binding by either unlabelled colchicine or test compound was calculated relative to the DMSO negative control.

Compounds of Formula (I) encompass vascular damaging agents and pro-drugs of vascular damaging agents. Pro-drugs of vascular damaging agents are believed to be cleaved in-vivo. Without being bound by theoretical considerations these pro-drugs may have lower activity in the in-vitro colchicine binding site competitive assay, than would be anticipated when the activity of these compounds is measured in cell based assays or in-vivo.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) yields are given for illustration only and are not necessarily the maximum attainable;

(iv) the structures of the end-products of the Formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) flash chromatography was performed on silica (Merck Keiselgel: Art.9385);

(vii) OASIS™ is a macroporous co-polymer, used to purify hydrophilic compounds, made form a balanced ratio of lipophilrc divinylbenzene and hydrophillic N-vinylpyr-rolidone. OASIS™ is described in the following patents, U.S. Pat. No. 5,882,521, U.S. Pat. No. 5,976,376 and U.S. Pat. No. 6,106,721. OASIS™ sample extraction products were obtained from Waters Corporation (Milford, Mass., USA).

(viii) HP20SS resin (DIAION® HP20SS) was obtained from Mitsubishi Chemical America Inc.

| Abbreviations | |
|---|---|
| 4-Dimethylaminopyridine | DMAP |
| 1-(3-Dimethylaminopropyl)-3-ethylcarbodiimide hydrochloride | EDCI |
| Dimethyl sulphoxide | DMSO |
| Trifluoroacetic acid | TFA |
| N-(9-fluorenylmethoxycarbonyl) | N-FMOC |
| N-tert-Butoxycarbonyl | N-Boc |
| Potassium tert-butylate | tBuOK |

EXAMPLE 1

5-(phenylsulfanyl)-1,3-dihydro-2H-indol-2-one

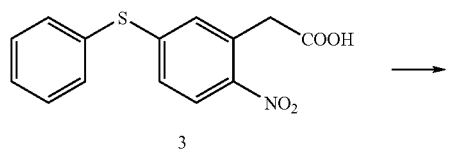

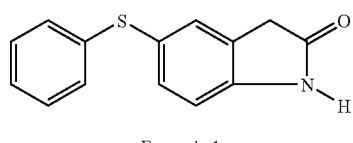

Example 1

A suspension of 3 (1.52 g; 5.2 mmol) and zinc (1.38 g; 21 mmol) in 50% $H_2SO_4$ (20 ml) and ethanol (30 ml) was heated at 100° C. for 10 hours. After evaporation of ethanol, the mixture was extracted with AcOEt and purified by flash chromatography eluting with $CH_2Cl_2$/EtOH 96/4 to give 5-(phenylsulfanyl)-1,3-dihydro-2H-indol-2-one.

Yield: 31% $^1$H NMR (CDCl$_3$): 3.52 (s, 2H); 6.84 (d, 1H); 7.1–7.4 (m, 7H); 8.04 (s, 1H). MS-ESI: 240 [M−H]$^-$ The starting material was prepared as follows:

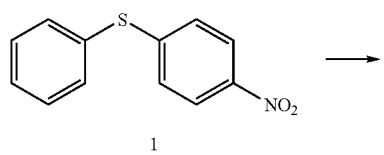

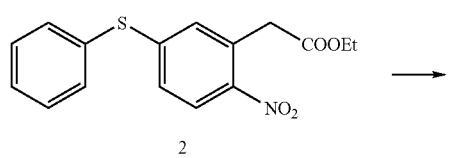

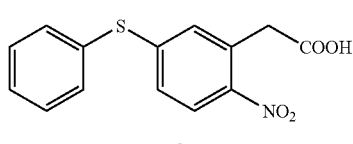

A suspension of t-BuOK (6.73 g; 60 mmol) in THF (70 ml) was cooled to −40° C. under argon and treated with a solution of 1 (5.78 g; 25 mmol) and ethyl chloroacetate (3.7 g; 30 mmol) in THF (30 ml). The mixture was stirred at −40° C. for 2 hours. HCl (2N; 40 ml) was added and the mixture was stirred at ambient temperature for 15 minutes and extracted with AcOEt/H$_2$O. The organic phase was evaporated and purified by flash chromatography eluting with petroleum ether/AcOEt 90/10 to give 2.

Yield: 33% $^1$H NMR spectrum (CDCl$_3$): 1.24 (t, 3H); 3.92 (s, 2H); 4.15 (q, 2H); 7.03 (d, 1H); 7.08 (dd, 1H); 7.43–7.48 (m, 3H); 7.52–7.56 (m, 2H); 8.01 (d, 1H). MS-ESI: 316 [M−H]$^-$ A solution of 2 (2.61 g; 8.2 mmol) in dioxan (25 ml) was treated with NaOH (2N, 5.4 ml) at ambient temperature for 5 hours. The solution was acidified to pH 2 with 6N HCl and extracted with AcOEt and purified by flash chromatography, eluting with $CH_2Cl_2$/EtOH 96/4 to give 3. Yield: 64% $^1$H NMR spectrum (CDCl$_3$): 3.96 (s, 2H); 1.01 (d, 1H); 7.09 (dd, 1H); 7.43–7.49 (m, 3H); 7.52–7.58 (m, 2H); 8.03 (d, 1H).

EXAMPLE 2

5-(4-aminophenoxy)-1,3-dihydro-2H-indol-2-one

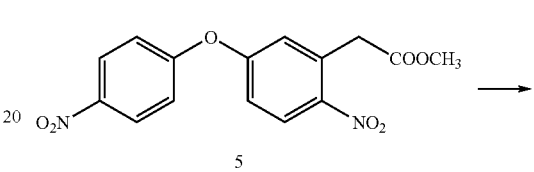

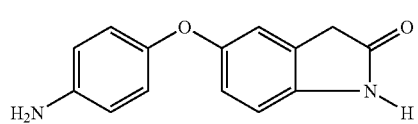

Example 2

Fe (0.387 g; 6.9 mmol) was added to a solution of 5 (0.4 g; 1.1 mmol) in AcOH (10 ml). The mixture was heated at 80° C. for 30 minutes and evaporated to dryness. The residue was taken up in water. The solution was adjusted to pH 7.5 with sat. NaHCO$_3$ and extracted with AcOEt. The residue was purified by flash chromatography eluting with $CH_2Cl_2$/MeOH 97/3 to give 5-(4-aminophenoxy)-1,3-dihydro-2H-indol-2-one.

Yield: 41% $^1$H NMR spectrum (CDCl$_3$): 3.43 (s, 2H); 4.89 (s, 2H); 6.55 (d, 2H); 6.66–6.76 (m, 4H); 6.78 (d, 1H); 10.24 (s, 1H). MS-ESI: 241 [M+H]$^+$ The starting material 5 was prepared from 4 as described in example 1. Yield: 28% $^1$HNMR spectrum (CDCl$_3$): 1.27 (t, 3H); 4.01 (s, 2H); 4.19 (q, 2H); 7.01 (d, 1H); 7.09 (dd, 1H); 7.18 (d, 2H); 8.22 (d, 1H); 8.30 (d, 2H).)

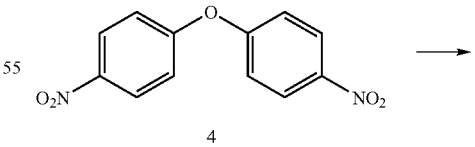

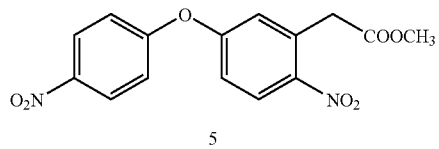

EXAMPLE 3

5-(4-aminophenylsulfanyl)-1,3-dihydro-2H-indol-2-one

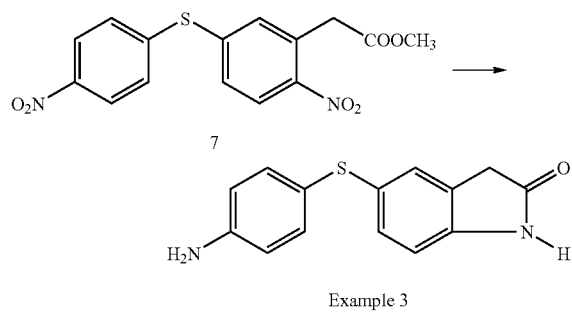

Example 3 was prepared as described for example 2 but using 7 in replacement of 5.

Yield: 14% $^1$H NMR spectrum (CDCl$_3$): 3.47 (s, 2H); 3.77 (s, 2H); 6.62 (d, 2H); 6.74 (d, 1H); 7.10 (s, 1H); 7.14 (d, 1H); 7.25 (d, 2H); 7.70 (d, 1H). MS-ESI: 255 [M–H]$^-$ The starting material 7 was prepared as described in example 2 for 5 starting from 6.

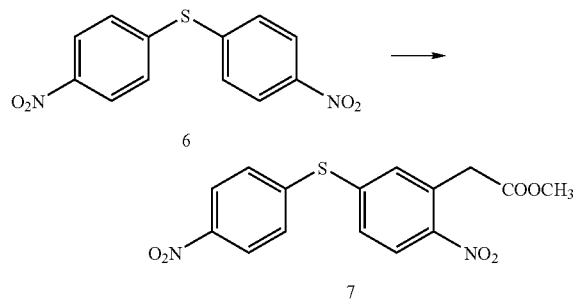

$^1$H NMR spectrum (CDCl$_3$): 1.27 (t, 3H); 3.98 (s, 2H); 4.18 (q, 2H); 7.3–7.7 (4H); 8–8.3 (m, 3H).

EXAMPLE 4

5-(4-N-glutaminylaminophenoxy)-1,3-dihydro-2H-indol-2-one

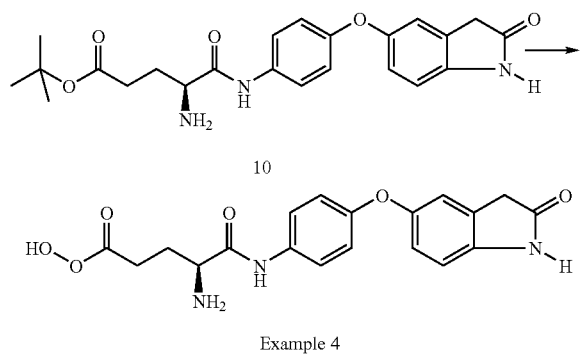

Example 4

A solution of 10 (0.2 g; 0.47 mmol) in solution in CH$_2$Cl$_2$ (1 ml) was treated with a solution of HCl (20%) in dioxan (2.5 ml). After stirring at ambient temperature for 2 hours the mixture was evaporated and purified on HP20SS resin, eluting with water to give 5-(4-N-glutaminylaminophenoxy)-1,3-dihydro-2H-indol-2-one.

Yield: 81% $^1$H NMR spectrum (DMSOd$_6$): 2.01–2.13 (m, 2H); 2.39 (t, 2H); 3.47 (s, 2H); 3.93–4.05 (m, 1H); 6.80 (d, 1H); 6.85 (dd, 1H); 6.93 (d, 1H); 6.96 (d, 2H); 7.58 (d, 2H); 8.34 (bs, 2H); 10.37 (s, 1H); 10.55 (s, 1H); 12.35 (bs, 1H). MS-ESI: 368 [M–H]$^-$

| Elemental analysis | Found | C 53.21 | H 5.05 | N 9.93 | Cl 7.96 |
|---|---|---|---|---|---|
| C$_{19}$H$_{19}$N$_3$O$_5$, 0.91 H$_2$O, 0.95 HCl | Requires | C 54.28 | H 5.22 | N 9.99 | Cl 8.01 |

The starting material was prepared as follows:

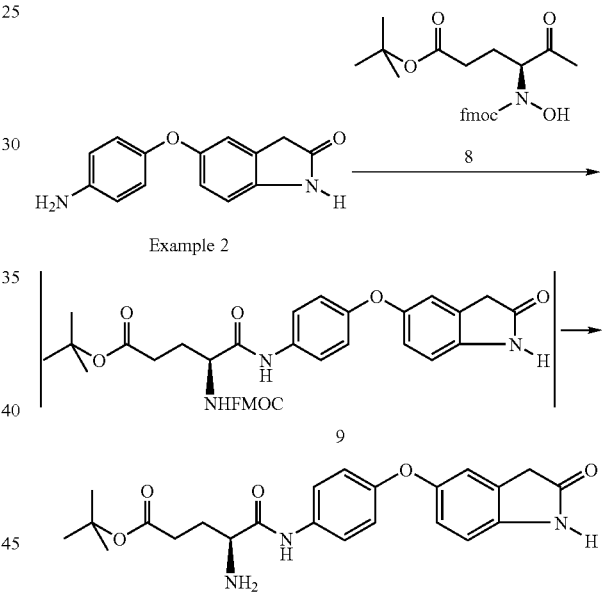

A solution of 5-(4-aminophenoxy)-1,3-dihydro-2H-indol-2-one (Example 2) (0.24 g; 1 mmol), 8 (0.638 g; 1.5 mmol), EDCI (0.288 g; 1.5 mmol) and DMAP (0.005 g; 0.02 mmol) in CH$_2$Cl$_2$ (7 ml) was stirred under argon for 2 hours. The mixture was purified by flash chromatography eluting with CH$_2$Cl$_2$/MeOH 98/2 to give 9 which was redissolved in CHCl$_3$ (3.5 ml) and treated with piperidine (1 ml). After stirring for 1 h 30, the mixture was diluted with water and extracted with CH$_2$Cl$_2$. The organic phase was purified by flash chromatography eluting with CH$_2$Cl$_2$/MeOH 95/5 to give 10.

Yield: 47%/ $^1$H NMR spectrum (DMSOd6): 1.39 (s, 9H); 1.59–1.72 (m, 1H); 1.80–1.92 (m, 1H); 2.21–2.39 (m, 2H); 3.25–3.33 (m, 2H); 3.46 (s, 2H); 6.79 (d, 1H); 6.83 (dd, 1H); 6.89–6.93 (m, 3H); 7.60 (d, 2H); 9.85 (bs, 1H); 10.33 (s, 1H). MS-ESI: 424 [M–H]$^-$

EXAMPLE 5

5-(4-N-Serylaminophenoxy)-1,3-dihydro-2H-indol-2-one

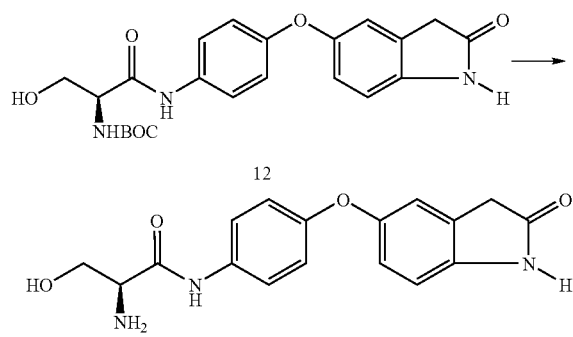

Example 5

A solution of 12 (0.21 g; 0.49 mmol) in $CH_2Cl_2$ (2 ml) was treated with a solution of HCl/dioxan (2,4 N; 2 ml). After stirring at ambient temperature for 2 h 30, the mixture was evaporated to dryness. The residue was taken up in water, DMF and purified on HP20SS resin after neutralisation to pH 7.5 with 0.5 N NaOH. After elution with $CH_3CN/H_2O$ 50/50, the appropriate fractions were acidified to pH 3 and freeze dried to give 5-(4-N-Serylaminophenoxy)-1,3-dihydro-2H-indol-2-one.

Yield: 64% $^1$H NMR spectrum (DMSOd$_6$): 3.47 (s, 2H); 3.81–3.87 (m, 2H); 3.99 (bs, 1H); 5.56 (bs, 1H); 6.80 (d, 1H); 6.84 (dd, 1H); 6.92 (s, 1H); 6.95 (d, 2H); 7.60 (d, 2H); 8.27 (bs, 2H); 10.36 (s, 1H); 10.61 (s, 1H). MS-ESI: 328 [M+H]$^+$ The starting material was prepared as follows:

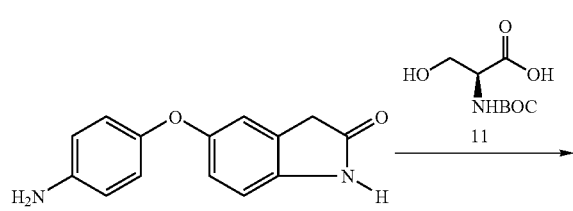

A solution of 5-(4-aminophenoxy)-1,3dihydro-2H-indol-2-one (Example 2) (0.24 g; 1 mmol), 11 (0.267 g; 1 mmol), EDCI (0.346 g; 1.8 mmol) and DMAP (0.020 g; 0.16 mmol) in $CH_2Cl_2$ (5 ml) was stirred under argon overnight. The mixture was purified by flash chromatography eluting with $CH_2Cl_2$/MeOH 97/3 to give 12.

Yield: 50% $^1$H NMR spectrum (DMSOd$_6$): 1.38 (s, 9H); 3.46 (s, 2H); 3.5 (bs, 2H); 4.07–4.18 (m, 1H); 4.92 (t, 1H); 6.73 (d, 1H); 6.78 (d, 1H); 6.82 (d, 1H); 6.88–6.95 (m, 3H); 7.58 (d, 2H); 9.91 (s, 1H); 10.32 (s, 1H).

EXAMPLE 6

5-(4-N-Glycylaminophenoxy)-1,3-dihydro-2H-indol-2-one

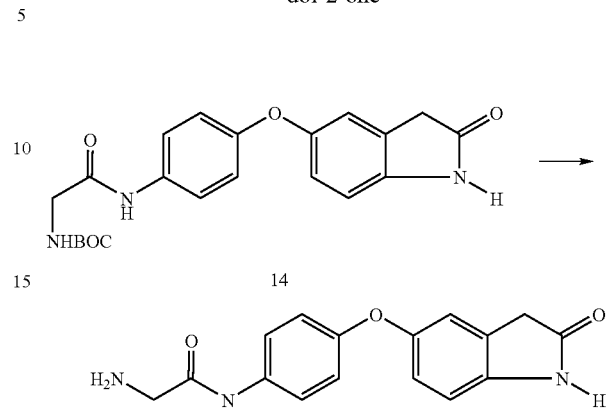

Example 6

A solution of 14 (0.681 g; 1.71 mmol) in $CH_2Cl_2$ (2 ml) was treated with a solution of HCl/dioxan (2.4 N; 6 ml). The mixture was stirred at ambient temperature for 1 hour and evaporated. The residue was taken up in DMF/$H_2O$, neutralised to pH 7 with 2N NaOH and purified on reverse phase silica eluting with a gradient of $CH_3CN/H_2O$. The appropriate fractions were acidified to pH 3.2 with 2N HCl and freezer dried to give 5-(4-N-Glycylaminophenoxy)-1,3-dihydro-2H-indol-2-one.

Yield: 43% $^1$H NMR spectrum (DMSOd6): 3.47 (s, 2H); 3.75 (s, 2H); 6.80 (d, 1H); 6.85 (dd, 1H); 6.93 (d, 1H); 6.95 (d, 2H); 7.57 (d, 2H); 8.15 (bs, 2H); 10.36 (s, 1H); 10.58 (s, 1H). MS-ESI: 298 [M+H]$^+$ The starting material was prepared as described for compound 12 but using 13 in replacement of 11.

Yield: 85% $^1$H NMR spectrum (DMSOd6):1.39 (s, 9H); 3.47 (s, 2H); 3.59 (d, 2H); 6.78 (d, 1H); 6.83 (dd, 1H); 6.89–6.95 (m, 3H); 7.03 (t, 1H); 7.54 (d, 2H); 9.88 (s, 1H); 10.32 (s, 1H).

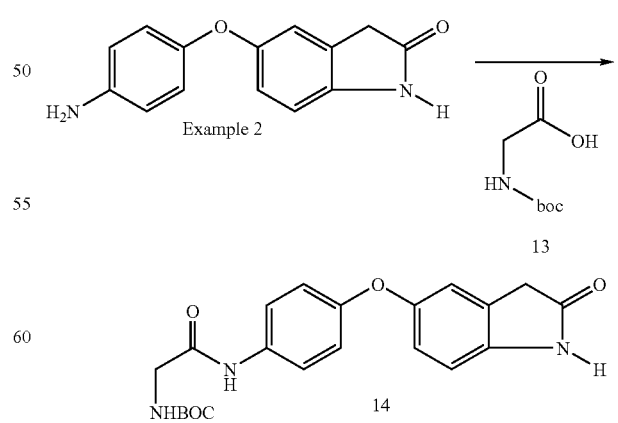

EXAMPLE 7

5-(4-N-glutaminylaminophenylsulfanyl-1,3-dihydro-2H-indol-2-one

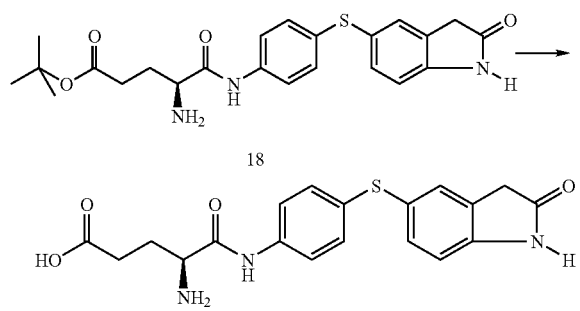

Example 7

The compound was prepared as described in example 4 (replacing 10 by 18).

Yield: 70% $^1$H NMR spectrum (DMSOd$_6$): 1.98–2.15 (m, 2H); 2.38 (t, 2H); 3.48 (s, 2H); 3.94–4.08 (m, 1H); 6.85 (d, 1H); 7.20–7.31 (m, 4H); 7.58 (d, 2H); 8.36 (bs, 2H); 10.54 (s, 1H); 10.80 (s, 1H); 12.30 (bs, 1H). MS-ESI: 384 [M–H]$^-$

| Elemental analysis | Found | C 51.31 | H 4.88 | N 9.35 | S 6.99 | Cl 6.84 |
|---|---|---|---|---|---|---|
| C$_{19}$H$_{19}$N$_3$O$_4$S, 1.33 H$_2$O 0.9 HCl | Requires | C 51.61 | H 5.14 | N 9.50 | S 7.25 | Cl 7.22 |

The starting material was prepared as described in example 4 starting from example 3.

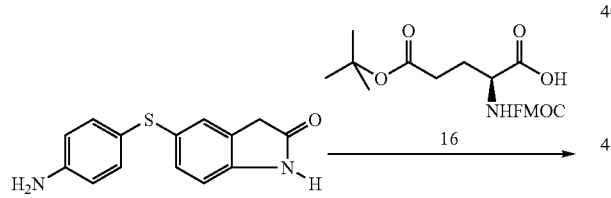

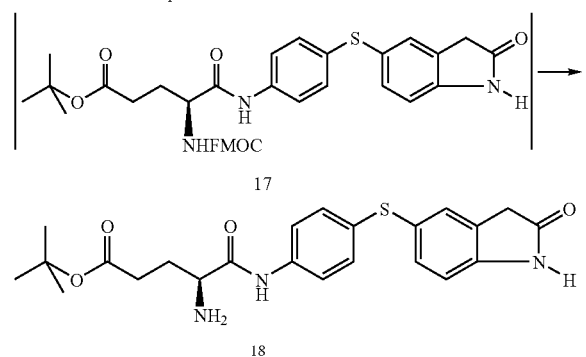

Yield: 44% $^1$H NMR spectrum (DMSOd$_6$): 1.38 (s, 9H); 1.58–1.69 (m, 1H); 1.74–1.91 (m, 1H); 2.23–2.36 (m, 2H); 3.47 (s, 2H); 6.82 (d, 2H); 7.18–7.27 (m, 4H); 7.61 (d, 2H); 10.50 (s, 1H).

EXAMPLE 8

5-(4-hydroxyphenylsulfanyl)-1,3-dihydro-2H-indol-2one

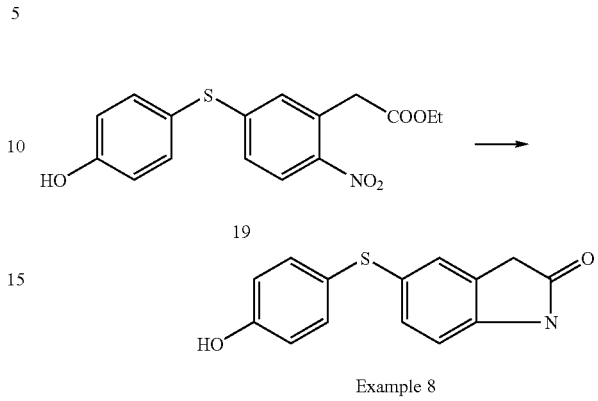

Example 8

5-(4-hydroxyphenylsulfanyl)-1,3-dihydro-2H-indol-2-one was prepared as described in example 1.

Yield: 30%. $^1$H NMR spectrum (DMSOd$_6$): 3.44 (s, 2H); 7.73–7.79 (m, 3H); 7.03–7.15 (m, 2H); 7.21 (d, 2H); 9.69 (s, 1H); 10.42 (s, 1H). MS-ESI: 256 [M–H]$^-$ The starting material was prepared as follows:

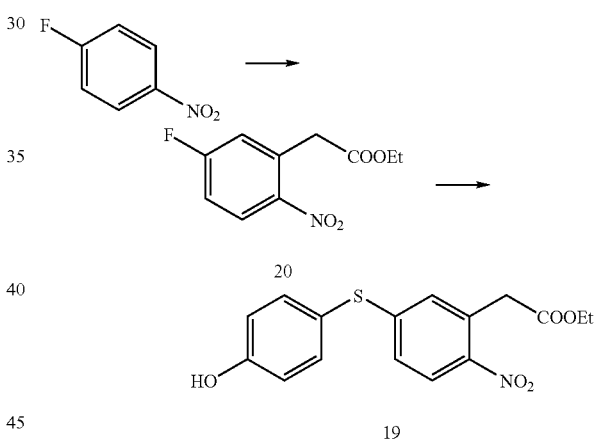

To a suspension of t-BuOK (22.44 g; 0.2 mmol) in THF (300 ml) at −40° C. under argon was added a solution of 4-fluoronitrobenzene (14.1 g; 0.1 mmol) and ethyl chloroacetate (14.7 g; 0.12 mmol) in THF (100 ml). After 1 hour at −40° C. the mixture was allowed to warm up at −5° C. and 2N HCl (200 ml) was added. After extraction with AcOEt/H$_2$O the organic phase was purified by flash chromatography eluting with petroleum ether/AcOEt to give 20. $^1$HNMR spectrum (CDCl$_3$): 1.27 (t, 3H); 4.01 (s, 2H); 4.19 (q, 2H); 7.07 (dd, 1H); 7.15 (dd., 1H); 8.20 (dd, 1H).

A mixture of 20 (2.27 g; 0.01 mmol), K$_2$CO$_3$ (2.07 g; 0.01 mmol), 4-mercaptophenol (1.5 g; 0.01 mmol) in N-methyl pyrrolidone (20 ml) was heated at 80° C. under argon atmosphere for 3 hours. After extraction with AcOEt/H$_2$O the organic phase was purified by flash chromatography eluting with petroleum ether/AcOEt 75/25 to give 19.

Yield: 81% $^1$H NMR spectrum (CDCl$_3$): 1.25 (t, 3H); 3.92 (s, 2H); 4.16 (q, 2H); 5.37 (s, 1H); 6.90 (d, 2H); 6.94 (d, 1H); 6.98 (dd, 1H); 7.43 (d, 2H); 7.99 (d, 1H).

EXAMPLE 9

6-benzyloxy-1,3-dihydro-2H-indol-2-one

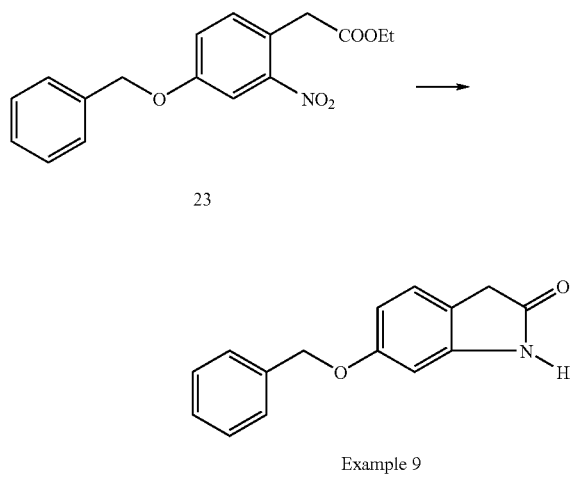

Example 9

5-benzyloxy-1,3-dihydro-2H-indol-2-one was prepared as described in example 2 but using 23 in replacement of 5.

Yield: 54% $^1$H NMR spectrum (CDCl$_3$): 3.47 (s, 2H); 5.06 (s, 2H); 6.53 (d, 1H); 6.62 (dd, 1H); 7.10 (d, 1H); 7.32–7.46 (m, 5H); 7.78 (bs, 1H). MS-ESI: 240 [M+H]$^+$ The starting material was prepared as follows:

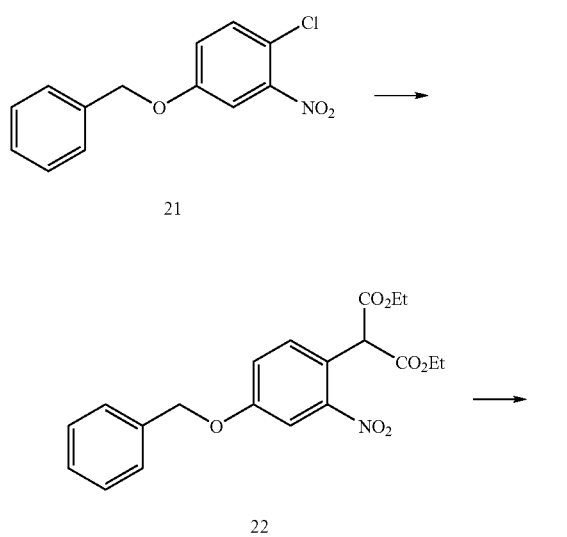

Diethylmalonate (3.78 g; 23.6 mmol) was added under argon atmosphere dropwise to a suspension of NaH 60% (0.91 g; 22.8 mmol) in DMSO (40 ml). The mixture was heated at 80° C. for 20 minutes. After cooling, 21 (2.7 g; 10 mmol) in solution in DMSO (10 ml) was added. The mixture was heated at 100° C. for 20 hours acetic acid (1.4 ml) was added and the mixture was extracted with CH$_2$Cl$_2$/0.5N HCl. The organic phase was evaporated and purified by flash chromatography eluting with petroleum ether/AcOEt 80/20 to give 22.

Yield: 68% $^1$H NMR spectrum (CDCl$_3$): 1.28 (t, 6H); 3.36 (s, 1H); 4.21 (q, 2H); 5.12 (s, 2H); 7.23 (dd, 1H); 7.35–7.45 (m, 6H); 7.66 (d, 1H).

A solution of 22 (2.73 g; 7 mmol) and LiCl (0.6 g; 14 mmol) in DMSO (30 ml) and H$_2$O (0.13 ml) was heated at 80° C. overnight. The mixture was extracted with AcOEt/sat NaCl to give after evaporation of the organic phase 23 as an oil which was used without further purification.

Yield: 32% $^1$H NMR spectrum (CDCl3): 1.25 (t, 3H); 3.93 (s, 2H); 4.20 (q, 2H); 5.12 (s, 2H); 7.17–7 (m, 3H); 7.35–7 (m, 4H); 7.65 (dd, 1H).

EXAMPLE 10

6-(3-aminobenzyloxy)-1,3-dihydro-2H-indol-2-one

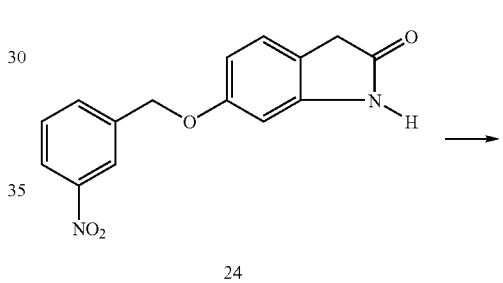

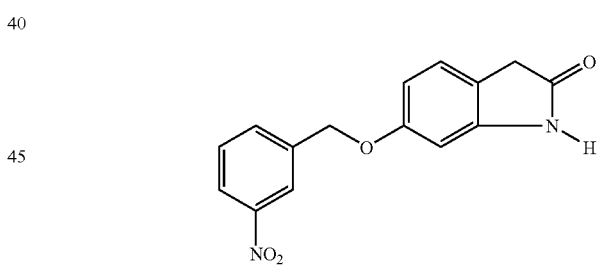

Example 10

A mixture of 24 (0.129 g; 0.454 mmol) and Fe (0.127 g; 2.27 mmol) in MeOH (3 ml) and 12N HCl (1 ml) was heated at 80° C. for 1 h 30. After evaporation and dilution with water, the mixture was neutralised to pH 7.5 with sat NaHCO$_3$ and extracted with AcOEt. The organic phase was evaporated and purified by flash chromatography eluting with petroleum ether/AcOEt 50/50 to give after evaporation an oil which was triturated with ether and pentane to give 6-(3-aminobenzyloxy)-1,3-dihydro-2H-indol-2-one as a solid.

Yield: 30% $^1$H NMR spectrum (DMSOd$_6$): 3.63 (s, 2H); 4.91 (s, 2H); 5.22 (bs, 2H); 6.42 (d, 1H); 6.48–6.57 (m, 3H); 6.62 (m, 1H); 7.01 (dd, 1H); 7.07 (d, 1H); 10.31 (s, 1H). MS-ESI: 255 [M+H]$^+$ The starting material was prepared as follows:

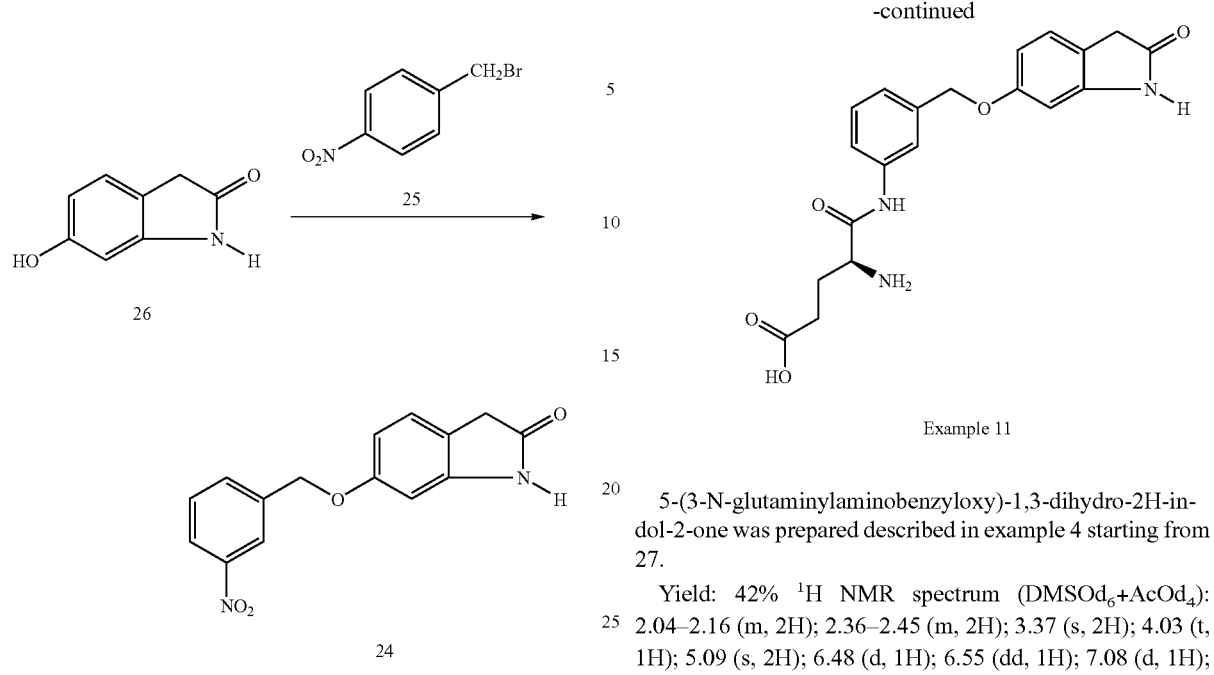

A mixture of 26 (0.224 g; 1.5 mmol), K$_2$CO$_3$ (0.228 g; 1.65 mmol) and 25 (0.558 g; 1.95 mmol) in DMF (4 ml) was stirred under argon atmosphere for 2 days. The mixture was extracted with H2O/AcOEt and the organic phase evaporated and purified by flash chromatography eluting with petroleum ether/AcOEt 30/70 to give 24.

Yield: 40% $^1$H NMR spectrum (DMSOd$_6$): 3.37 (s 2H); 5.25 (s, 2H); 6.49 (d, 1H); 6.60 (dd, 1H); 7.11 (d, 1H); 7.71 (dd, 1H); 7.91 (d, 1H); 8.20 (d, 1H); 8.30 (s, 1H); 10.38 (s, 1H).

EXAMPLE 11

5-(3-N-glutaminylaminobenzyloxy)-1,3-dihydro-2H-indol-2-one 5-(3-N-glutaminylaminobenzyloxy)-1,3-dihydro-2H-indol-2-one was prepared described in example 4 starting from 27.

Yield: 42% $^1$H NMR spectrum (DMSOd$_6$+AcOd$_4$): 2.04–2.16 (m, 2H); 2.36–2.45 (m, 2H); 3.37 (s, 2H); 4.03 (t, 1H); 5.09 (s, 2H); 6.48 (d, 1H); 6.55 (dd, 1H); 7.08 (d, 1H); 7.19 (d, 1H); 7.37 (dd, 1H); 7.60 (d, 1H); 7.69 (d, 1H); 10.30 (s, 1H); 10.64 (s, 1H). MS-ESI: 382 [M−H]$^-$ The starting material was prepared using the same method as described for 10 in Example 4 but starting from 6-(3-aminobenzyloxy)-1,3-dihydro-2H-indol-2-one (Example 10.)

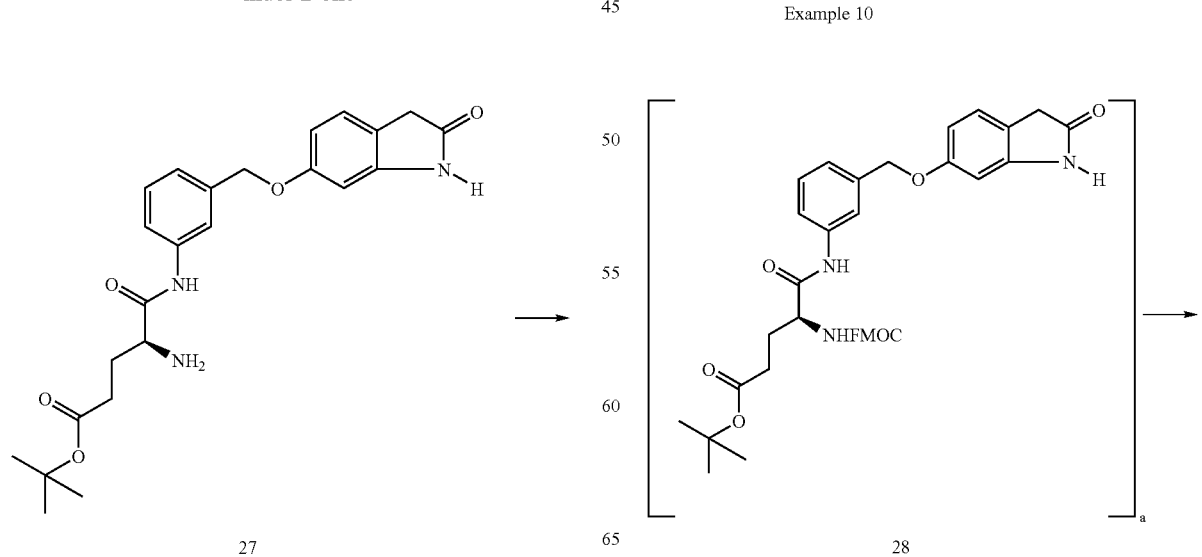

-continued

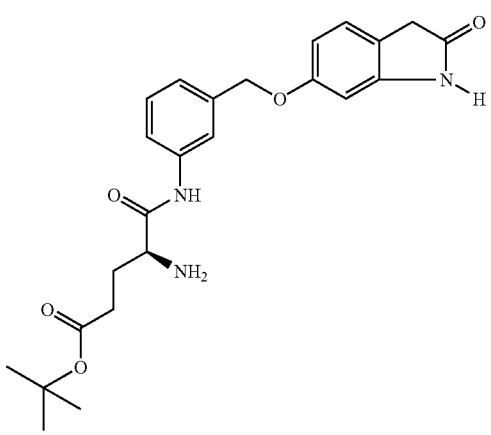

27

Yield: 69% ¹H NMR spectrum (DMSOd₆): 1.4(s, 9H); 1.8–1.96 (m, 21); 2.27–2.34 (m, 2H); 3.38 (s, 2H); 4.08–4.31 (m, 3H); 5.07 (s, 2H); 6.46 (d, 1H); 6.56 (dd, 1H); 7.08–7.14 (m, 2H); 7.31–7.45 (m, 4H); 7.58 (d; 1H); 7.68–7.77 (m, 3H); 7.91 (d, 2H); 10.09 (s, 1H); 10.33 (s, 1H)

EXAMPLE 12

6-benzyloxy-N-methyl-1,3-dihydro-2H-indol2-one

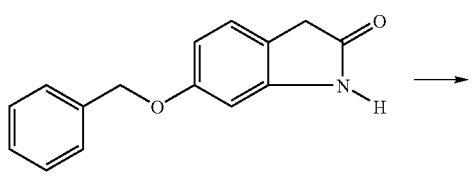

Example 9

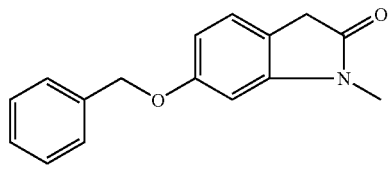

Example 12

A mixture of 6-benzyloxy-1,3-dihydro-2H-indol-2-one (Example 9) (0.12 g; 0.5 mmol), K₂CO₃ (0.07 g; 0.5 mmol) and CH₃I (0.031 ml) in acetone (5 ml) was refluxed under argon atmosphere for 6 hours. After evaporation to dryness, the residue was purified by flash chromatography eluting with petroleum ether/AcOEt 60/40 to give 6-benzyloxy-N-methyl-1,3-dihydro-2H-indol-2-one.

Yield: 31% ¹H NMR spectrum: 3.17 (s, 3H); 3.46 (s, 2H); 5.09 (s, 2H); 6.50 (d, 1H); 6.62 (dd, 1H); 7.12 (d, 1H); 7.31–7.49 (m, 5H). MS-ESI: 254 [M+H]⁺

EXAMPLE 13

4-benzyloxy-1,3-dihydro-2H-indol-2-one

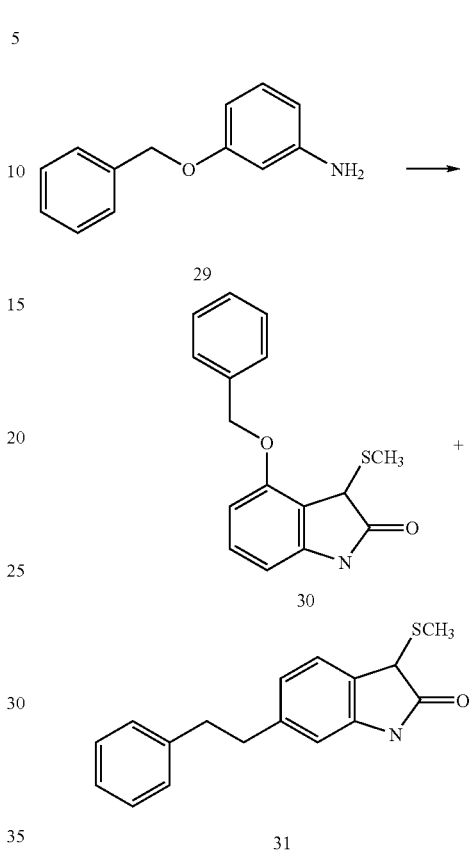

Example 13

To a solution of chlorine (1.47 g; 0.021 mmol) in CH₂Cl₂ (37 ml) at −70° C. was added under argon ethyl methylthioacetate (2 ml; 0.021 mmol) in CH₂Cl₂ (10 ml). After stirring for 5 minutes, 29 (8.35 g; 0.042 mmol) in solution in CH₂Cl₂ (40 ml) was added dropwise. The mixture was stirred at −70° C. for 1 hour, triethylamine (4.68 ml; 0.034 mmol) was added. After 30 minutes, the mixture was extracted, the organic phase was evaporated and purified by flash chromatography, eluting with CH₂Cl₂/AcOEt 90/10 to give a mixture of 30 and 31, as a side product The mixture of 30 and 31 (0.74 g; 2.59 mmol) in solution in EtOH (20 ml) was treated with Ni Raney (2 g) at room temperature for 2 hours. After filtration of the catalyst, the filtrate was evaporated and purified by flash chromatography, eluting with petroleum ether/AcOEt 60/40 to give 4-benzyloxy-1,3-dihydro-2H-indol-2-one. ¹H NMR spectrum (CDCl₃): 3.53 (s, 2H); 5.1 (s, 2H); 6.5–6.7 (m, 2H); 7.1–7.5 (m, 6H). MS-ES: 240 [M+H]⁺

EXAMPLE 14

5-(4-phosphonophenylsulfanyl)-1,3-dihydro-2H-indol-2-one

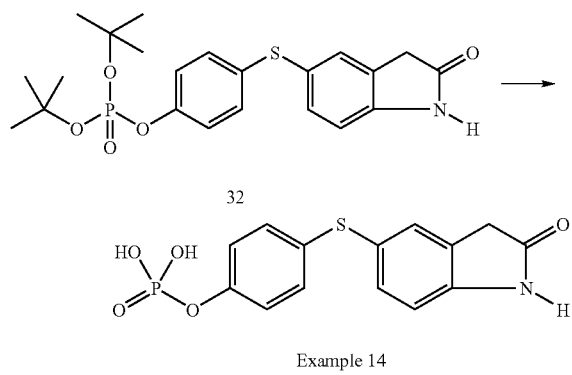

Example 14

A solution of 32 (0.275 g; 0.6 mmol) and TFA (1.5 ml) in CH$_2$Cl$_2$ (15 ml) was stirred at 0° C. for 10 minutes and at room temperature for 15 minutes. After evaporation to dryness, the residue was purified on OASIS resin eluting with a gradient of CH$_3$CN/H$_2$O 0–30% to give 5-(4-phosphonophenylsulfanyl)-1,3-dihydro-2H-indol-2-one.

Yield: 63% $^1$H NMR Spectrum (DMSOd$_6$+AcOD$_4$): 3.48 (s, 2H); 6.85 (d, 1H); 7.1–7.4 (m, 7H). MS-ESI: 336 [M–H]$^-$

| Elemental analysis | Found | C 49.10 | H 3.68 | N 4.45 | S 9.19 |
|---|---|---|---|---|---|
| C$_{14}$H$_{12}$NO$_5$SP, 0.3 H$_2$O | Requires | C 49.07 | H 3.71 | N 4.09 | S 9.36 |

The starting material was prepared as follows:

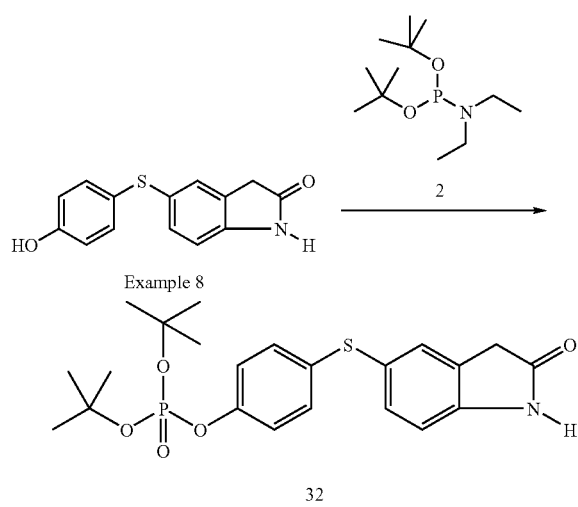

To a solution of 5-(4-hydroxyphenylsulfanyl)-1,3-dihydro-2H-indol-2-one (Example 8) (0.257 g; 1 mmol) and 1H-tetrazole (0.21 g; 3 mmol) in a mixture of DMF (2 ml) and THF (2 ml) was added under argon atmosphere di-tert-butyl diethylphosphoramidite (560 µl; 2 mmol). After stirring for one hour, the mixture was cooled to –70° C. and magnesium peroxyphtalate (0.544 g; 1.1 mmol) was added portionwise. The mixture was stirred at –70° C. for one hour and sat NaHCO$_3$ (15 ml) was added. After 15 minutes, the mixture was extracted with AcOEt. The organic phase was evaporated and purified by flash chromatography eluting with CH$_2$Cl$_2$/EtOH 98/2 to give 1.

Yield: 61% $^1$H NMR Spectrum (DMSOd$_6$): 1.44 (m, 9H); 3.50 (s, 2H); 6.86 (d, 1H); 7.1–7.4 (m, 6H). MS-ESI: 448 [M–H]$^-$

The invention claimed is:

1. A method of treatment, in a warm-blooded animal, to inhibit and/or reverse and/or alleviate symptom of angiogenesis and/or any disease state associated with angiogenesis comprising administering to said warm-blooded animal a therapeutically effective amount of a compound of Formula (I), wherein:

Formula (I)

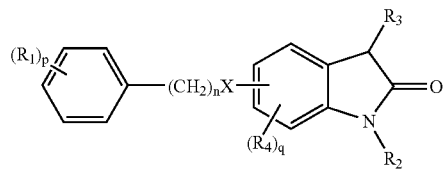

X is selected from: —O—, —S—, —S(O)—, —S(O$_2$)—, —N(R$_5$)—, —C(O)—, —C(O)N(R$_5$)— or —N(R$_5$)C(O);

R$_1$ is independently selected from: amino, halo, hydroxy, —OPO$_3$H$_2$, C$_{1-4}$alkyl, or C$_{1-4}$alkoxy, wherein the amino group is optionally substituted by an amino acid residue and the hydroxy group is optionally esterified;

R$_2$ is selected from: hydrogen or C$_{1-4}$alkyl;

R$_3$ is selected from: hydrogen, halo, hydroxy, hydroxy C$_{1-14}$alkyl, cyano, cyanoC$_{1-4}$alkyl, carboxy, carboxyC$_{1-4}$alkyl, C$_{1-4}$alkanoyl, C$_{1-4}$alkanoylC$_{1-4}$alkyl, carbamoyl, carbamoylC$_{1-4}$alkyl, C$_{1-4}$alkoxy, C$_{1-4}$alkoxycarbonyl, C$_{1-4}$alkoxycarbonylC$_{1-4}$alkyl, C$_{1-4}$alkoxycarbonylamino, amino, N—C$_{1-4}$alkylamino, NN-diC$_{1-4}$alkylamino, aminoC$_{1-4}$alkyl, N—C$_{1-4}$alkylaminoC$_{1-4}$alkyl, NN-diC$_{1-4}$alkylaminoC$_{1-4}$alkyl, ureido, or C$_{1-4}$alkylureyleno;

R$_4$ is independently selected from: C$_{1-4}$alkyl, C$_{1-4}$alkoxy or halo;

R$_5$ is selected from: hydrogen or C$_{1-4}$alkyl;

n is 0 or 1;

p is 0, 1, 2, or 3; and q is 0, 1 or 2;

or a salt, pro-drug or solvate thereof.

2. The method according to claim 1, or a salt, pro-drug or solvate thereof, wherein X is —O—, —S—, —S(O)—, or —S(O$_2$)—.

3. The method according to claim 1 or claim 2, or a salt, pro-drug or solvate thereof, wherein R$^3$ is hydrogen.

4. The method according to claim 1, or a salt, pro-drug or solvate thereof, wherein R$^1$ is amino, hydroxy, —OPO$_3$H$_2$, or C$_{1-4}$alkoxy, wherein the amino group is optionally substituted by an amino acid residue and the hydroxy group is optionally esterified.

5. The method according to claim 4, or a salt, pro-drug or solvate thereof, wherein R$^1$ is amino substituted by an amino acid residue or is an esterified hydroxy group.

6. The method according to claim 5, or a salt, pro-drug or solvate thereof, wherein R$^1$ is amino substituted by an amino acid residue and the amino acid residue is derived from glutamic acid, serine, threonine, arginine, glycine, alanine, β-alanine or lysine.

7. The method according to claim 4, or a salt, pro-drug or solvate thereof, wherein $R^1$ is $C_{1-4}$alkoxy.

8. A compound of Formula (IIa):

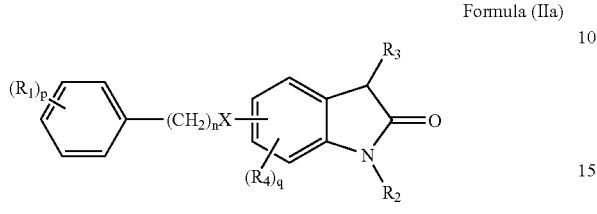

Formula (IIa)

wherein: n, q, X, $R_2$, $R_3$, $R_4$ and $R_5$ are as defined in claim 1; and p is 1, 2 or 3
$R_1$ is independently selected from: amino, halo, hydroxy, —OPO$_3$H$_2$ or $C_{1-4}$alkoxy, wherein the amino group is optionally substituted by an amino acid residue and the hydroxy group is optionally esterified;
with the proviso that:
  (i) when p is 1, $R_1$ cannot be halo or methyl, and when p is 2, $(R_1)_n$ cannot be di-halo or di-methyl;
  (ii) when is X is —N($R_5$)S(O$_2$)—, —N($R_5$)C(O)— or —C(O)—, n is 0 or 1, $R_2$ is hydrogen, $R_3$ is hydrogen, q is 1 and $R_4$ is 5-chloro and $R^5$ is hydrogen, then $(R_1)_p$, cannot be 2-methoxy, 3-methoxy, 4-methoxy, 4-nitro, 4-hydroxy, 4-amino, 3-chloro-4-methoxy or 3-chloro-4-ethoxy; and
  (ii) when X is linked at the 7-position of the oxindole ring, X is —O—, n is 0, $R_2$ is hydrogen, $R_3$ is hydrogen or methyl and q is 0, then $(R_1)_p$ cannot be 2-methoxy, 2-amino, or 3,4,5-tri-methoxy;
or salt, pro-drug or solvate thereof.

9. A compound of Formula (III), wherein:

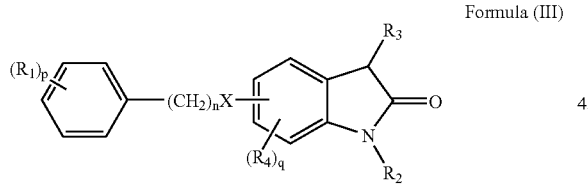

Formula (III)

X is selected from: —S—, —S(O)—, or —S(O$_2$)—;
and wherein $R^2$, $R^3$, $R^4$, r, p and q are as defined in claim 1; and
$R_1$ is independently selected from: amino, halo, hydroxy, —OPO$_3$H$_2$, or $C_{1-4}$alkoxy, wherein the amino group is optionally substituted by an amino acid residue and the hydroxy group is optionally esterified; with the proviso that the following compounds are excluded:
7-(phenylsulfanyl)-1,3-dihydro-2H-indol-2-one;
7-(2-chlorophenylsulfanyl)-1,3-dihydro-2H-indol-2-one;
7-(4-chlorophenylsulfanyl)-1,3-dihydro-2H-indol-2-one;
7-(benzylsulfanyl)-1,3-dihydro-2H-indol-2-one;
7-(phenylsulfinyl)-1,3-dihydro-2H-indol-2-one;
7-(2-chlorophenylsulfinyl)-1,3-dihydro-2H-indol-2-one;
7-(4-chlorophenylsulfinyl)-1,3-dihydro-2H-indol-2-one;
7-(phenylsulfonyl)-1,3-dihydro-2H-indol-2-one; and
7-(4-chlorophenylsulfinyl)-1,3-dihydro-2H-indol-2-one;

or a salt, pro-drug or solvate thereof.

10. A compound of Formula (V), wherein:

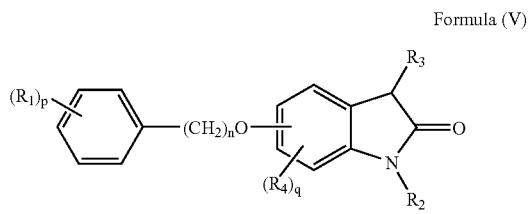

Formula (V)

wherein $R^1$, $R^2$, $R^3$, $R^4$, $R_5$, n and q are as defined in claim 1; and p is 1, 2 or 3;
with the proviso that:
  (i) when —(CH$_2$)$_n$O— is linked at the 4-position of the oxindole ring, n is 0, p is 0 and $R_2$ and $R_3$ are each independently hydrogen and q is 1 then $R_4$ cannot be 7-chloro;
  (ii) when —(CH$_2$)$_n$O— is linked at the 5-position of the oxindole ring, n is 0 or 1, $R_2$ is hydrogen or methyl, $R_3$ is hydrogen and q is 0, then p cannot be 0 and $(R_1)_p$ cannot be 2-chloro or 4-chloro;
  (iii) when —(CH$_2$)$_n$O— is linked at the 6-position of the oxindole ring, n is 1, p is 0, $R_2$ is hydrogen or methyl, $R_3$ is hydrogen and q is 1 then $R_4$ cannot be 5-methoxy; and
  (iv) when —(CH$_2$)$_n$O— is linked at the 7-position of the oxindole ring, n is 0 or 1, $R_2$ is hydrogen or methyl, $R_3$ is hydrogen and q is 0, then p cannot be 0 and $(R_1)_p$ cannot be 2-chloro, 2-fluoro, 2-amino, 2,6-dichloro or 3,4,5-trimethoxy;
or a salt, pro-drug or solvate thereof.

11. A compound according to claim 8 or claim 9, or a salt, pro-drug or solvate thereof, wherein $R^3$ is hydrogen.

12. A compound according to any one of claims 8 to 10, or a salt, pro-drug or solvate thereof, wherein $R^1$ is amino, hydroxy, —OPO$_3$H$_2$, or $C_{1-4}$alkoxy, wherein the amino group is optionally substituted by an amino acid residue and the hydroxy group is optionally esterified.

13. A compound according to claim 12, or a salt, pro-drug or solvate thereof wherein $R^1$ is amino substituted by an amino acid residue or $C_{1-4}$alkoxy.

14. A compound according to claim 13, or a salt, pro-drug or solvate thereof, wherein $R^1$ is amino substituted by an amino acid residue and the amino acid residue is derived from glutamic acid, serine, threonine, arginine, glycine, alanine, β-alanine or lysine.

15. A compound according to claim 12, or a salt, pro-drug or solvate thereof, wherein $R^1$ is $C_{1-4}$alkoxy.

16. A compound selected from:
5(phenylsulfanyl)-1,3-dihydro-2H-indol-2-one;
5-(4-aminophenoxy)-1,3-dihydro-2H-indol-2-one;
5-(4-aminophenylsulfanyl)-1,3-dihydro-2H-indol-2-one;
5-(4-hydroxyphenylsulfany)-1,3-dihydro-2H-indol-2-one; and
6-(3-aminobenzyloxy)-1,3-dihydro-2H-indol-2-one;
5-(4-N-glutaminylaminophenoxy)-1,3-dihydro-2H-indol-2-one;

5-(4-N-Serylaminophenoxy)-1,3-dihydro-2H-indol-2-one;

5-(4-N-Glycylaminophenoxy)-1,3-dihydro-2H-indol-2-one;

5-(4-N-glutaminylaminophenylsulfanyl-1,3-dihydro-2H-indol-2-one;

5-(3-N-glutaminylaminobenzyloxy)-1,3-dihydro-2H-indol-2-one; and 5-(4-phosphonophenylsulfanyl)-1,3-dihydro-2H-indol-2-one;

or a salt, prodrug or solvate thereof.

17. A pharmaceutical composition comprising a compound according to any one of claims 8 to 16 or a pharmaceutically-acceptable salt, pro-drug, or salvate thereof, in admixture with a pharmaceutically-acceptable diluent or carrier.

18. A method for the treatment of a cancer involving a solid tumour in a warm-blooded animal such as a human, which comprises administering to said animal in divided doses an effective amount of a compound of Formula (I), or salt, pro-drug or solvate thereof as claimed in claim 1.

19. A process for preparing a compound of Formula (I), or salt, pro-drug or solvate thereof, which process (wherein n, p, q, X, $R_1$, $R_2$, $R_3$, $R_4$ and $R_5$ are unless otherwise specified as defined in claim 1) comprising:

a) for compounds of Formula (I) wherein X is —O—, —S— or —N($R_5$)—, reacting a compound of Formula (A) with a compound of Formula (B),

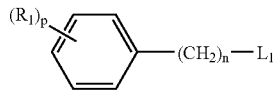

Formula (A)

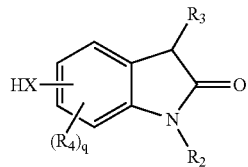

Formula (B)

wherein $L_1$ is a leaving group;

b) for compounds of Formula (I) wherein $R_2$ is hydrogen, reduction of a compound of Formula (C), wherein $R_6$ hydrogen or an alkyl chain,

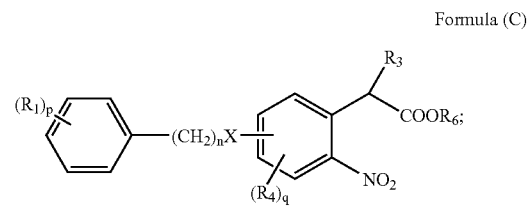

Formula (C)

c) for compounds of Formula (I) wherein $R_2$ is $C_{1-4}$alkyl, reacting a compound of Formula (I) wherein $R_2$ is hydrogen with a suitable alkylhalide;

d) for compounds of Formula (I) wherein $R_2$ is hydrogen and $R_3$ is hydrogen reacting a compound of Formula (D) with an alkylthioacetate, followed by reduction,

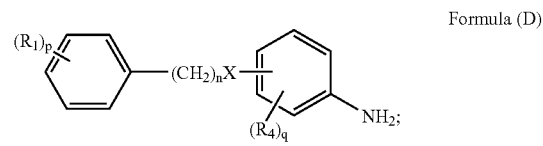

Formula (D)

e) for compounds of Formula (I) wherein X is —S(O)—, —S($O_2$)—, oxidising a compound of Formula (J),

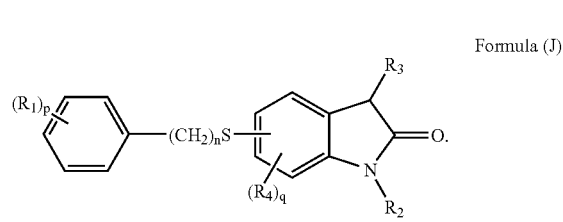

Formula (J)

and thereafter if necessary:

i) converting a compound of the Formula (I) into another compound of the Formula (I);

ii) removing any protecting groups;

iii) forming a salt, pro-drug or solvate.

* * * * *